(12) United States Patent
Kalia et al.

(10) Patent No.: US 11,854,676 B2
(45) Date of Patent: Dec. 26, 2023

(54) PROVIDING LIVE FIRST AID RESPONSE GUIDANCE USING A MACHINE LEARNING BASED COGNITIVE AID PLANNER

(71) Applicant: International Business Machines Corporation, Armonk, NY (US)

(72) Inventors: Anup Kalia, Elmsford, NY (US); Maja Vukovic, New York, NY (US); Michael S. Gordon, Yorktown Heights, NY (US); Komminist Weldemariam, Ottawa (CA)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 192 days.

(21) Appl. No.: 16/569,032

(22) Filed: Sep. 12, 2019

(65) Prior Publication Data
US 2021/0082554 A1 Mar. 18, 2021

(51) Int. Cl.
G16H 20/00 (2018.01)
G16H 50/70 (2018.01)
G16H 50/30 (2018.01)
G06N 20/00 (2019.01)

(52) U.S. Cl.
CPC ............. *G16H 20/00* (2018.01); *G06N 20/00* (2019.01); *G16H 50/30* (2018.01); *G16H 50/70* (2018.01)

(58) Field of Classification Search
CPC .................................................... A61B 5/4824
See application file for complete search history.

(56) References Cited

U.S. PATENT DOCUMENTS

| 10,716,517 B1 * | 7/2020 | McNair | A61B 5/1128 |
|---|---|---|---|
| 10,946,311 B1 * | 3/2021 | McNair | G16H 15/00 |
| 2011/0119212 A1 * | 5/2011 | De Bruin | A61B 5/369 706/12 |
| 2012/0226113 A1 * | 9/2012 | Pandya | G16H 50/30 600/301 |
| 2012/0230557 A1 | 9/2012 | Calman et al. | |

(Continued)

FOREIGN PATENT DOCUMENTS

CN 108498078 9/2018
CN 109065151 A * 12/2018
(Continued)

OTHER PUBLICATIONS

Wallis et al., A Smartphone App and Cloud-Based Consultation System for Burn Injury Emergency Care, Feb. 26, 2016, PLOS ONE (Year: 2016).*

(Continued)

*Primary Examiner* — Karen A Hranek
(74) *Attorney, Agent, or Firm* — Amin, Turocy & Watson, LLP

(57) ABSTRACT

Techniques are described for providing live first aid response guidance using a machine learning based cognitive aid planner. In one embodiment, a computer-implemented method is provided that comprises classifying, by a system operatively coupled to a processor, a type of an injury endured by a patient. The method further comprises, employing, by the system, one or more machine learning models to estimate a risk level associated with the injury based on the type of the injury and a current context of the patient.

19 Claims, 15 Drawing Sheets

(56) References Cited

U.S. PATENT DOCUMENTS

| | | | | |
|---|---|---|---|---|
| 2013/0218588 | A1* | 8/2013 | Kehr | A61J 7/0481 |
| | | | | 705/2 |
| 2013/0262357 | A1* | 10/2013 | Amarasingham | G16H 50/70 |
| | | | | 706/21 |
| 2014/0025394 | A1* | 1/2014 | Aoki | G16H 40/67 |
| | | | | 705/2 |
| 2014/0081659 | A1* | 3/2014 | Nawana | A61B 5/1118 |
| | | | | 705/3 |
| 2014/0088402 | A1 | 3/2014 | Xu | |
| 2014/0316242 | A1 | 10/2014 | Musahl et al. | |
| 2015/0087257 | A1 | 3/2015 | Balram et al. | |
| 2016/0129186 | A1* | 5/2016 | Douglas | G16H 40/63 |
| | | | | 601/84 |
| 2017/0367580 | A1* | 12/2017 | DiMaio | A61B 5/0064 |
| 2018/0060495 | A1* | 3/2018 | Mahapatra | G16H 50/50 |
| 2018/0075597 | A1* | 3/2018 | Zhou | G06N 20/00 |
| 2018/0140835 | A1* | 5/2018 | Sharma | G16H 40/63 |
| 2018/0182475 | A1* | 6/2018 | Cossler | G16H 50/50 |
| 2018/0193652 | A1* | 7/2018 | Srivastava | A61B 5/4848 |
| 2018/0315182 | A1* | 11/2018 | Rapaka | G16H 50/70 |
| 2018/0322956 | A1* | 11/2018 | Constantine | G16B 20/20 |
| 2019/0021677 | A1* | 1/2019 | Grbic | A61B 5/7292 |
| 2019/0139631 | A1* | 5/2019 | Eshelman | G16H 40/20 |
| 2019/0163873 | A1* | 5/2019 | Govindjee | G06Q 50/22 |
| 2019/0307384 | A1* | 10/2019 | Baeuerle | A61B 5/0533 |
| 2019/0313966 | A1* | 10/2019 | Lanzkowsky | A61B 5/0077 |
| 2019/0320974 | A1* | 10/2019 | Alzamzmi | G16H 50/20 |
| 2019/0388002 | A1* | 12/2019 | Bozsak | G16B 40/20 |
| 2020/0219611 | A1* | 7/2020 | Nag | G06N 7/005 |
| 2020/0234825 | A1* | 7/2020 | Dobson | G16H 80/00 |
| 2021/0027897 | A1* | 1/2021 | Rasochova | A63F 13/65 |
| 2021/0145359 | A1* | 5/2021 | Hunt | A61B 5/746 |

FOREIGN PATENT DOCUMENTS

| | | | | |
|---|---|---|---|---|
| CN | 109585020 | A * | 4/2019 | G16H 50/20 |
| JP | 2002177348 | A * | 6/2002 | |
| WO | 2015066297 | | 5/2015 | |
| WO | 2017067437 | A1 | 4/2017 | |

OTHER PUBLICATIONS

Karpathy et al., Large-sclae Video Classification with Convolutional Neural Networks, 2014, Computer Vision Foundation (Year: 2014).*

Petscharnig et al., Early and Late Fusion of Temporal Information for Classification of Surgical Actions in Laparoscopic Gynecology, 2018, IEEE 31st International Symposium on Computer-Based Medical Systems (Year: 2018).*

Rodriguez-Moreno et al., Video Activity Recognition: State-of-the-Art, Jul. 2019, Sensors 19 (Year: 2019).*

BabyCenter Staff. "Common childhood accidents and how to prevent them" Baby Center last web accessed on May 28, 2019 https://www.babycenter.com/0_common-childhood-accidents-and-how-to-prevent-them_403.bc (2016).

Karpathy et al., "Large-scale video classification with convolutional neural networks". (2014).

Krizhevsky et al., "ImageNet classification with deep convolutional neural networks" (2012).

* cited by examiner

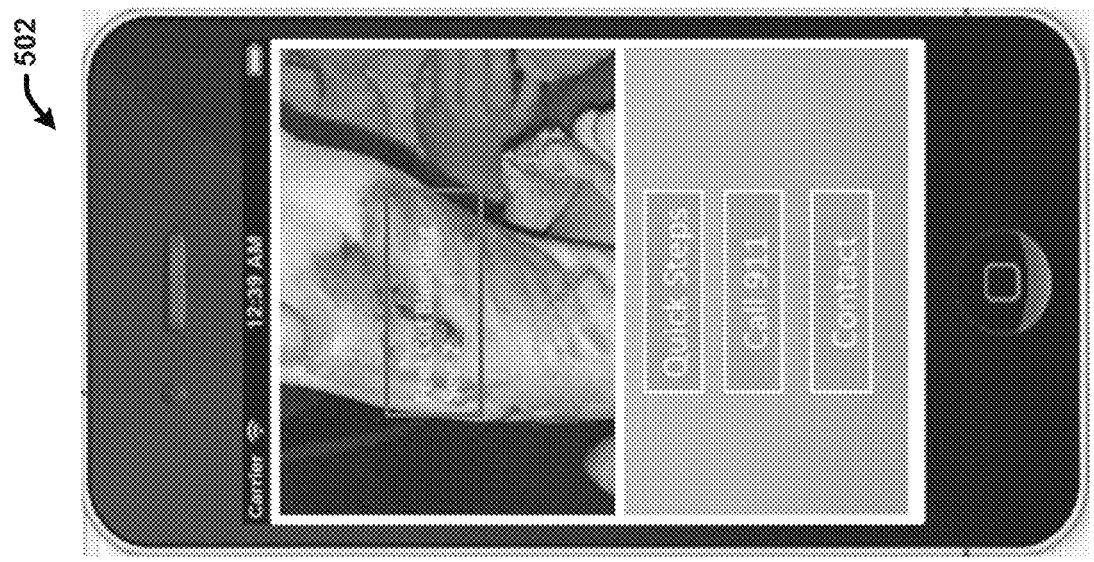
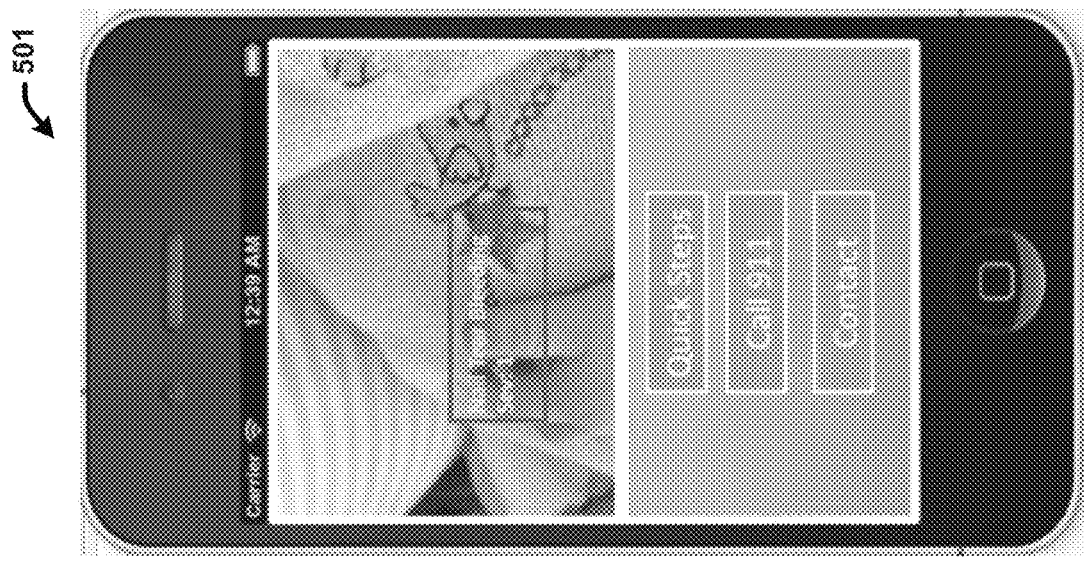
FIG. 5A

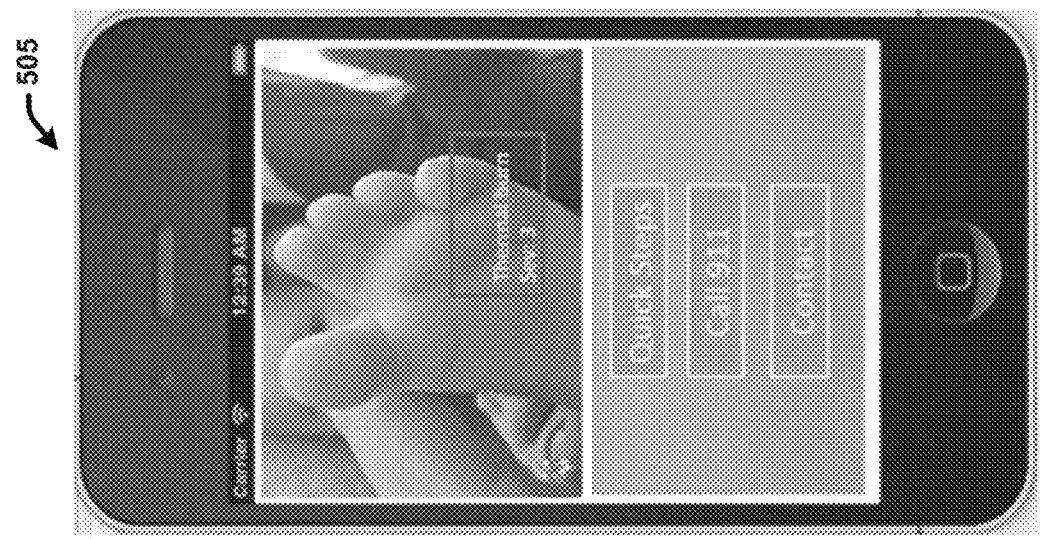
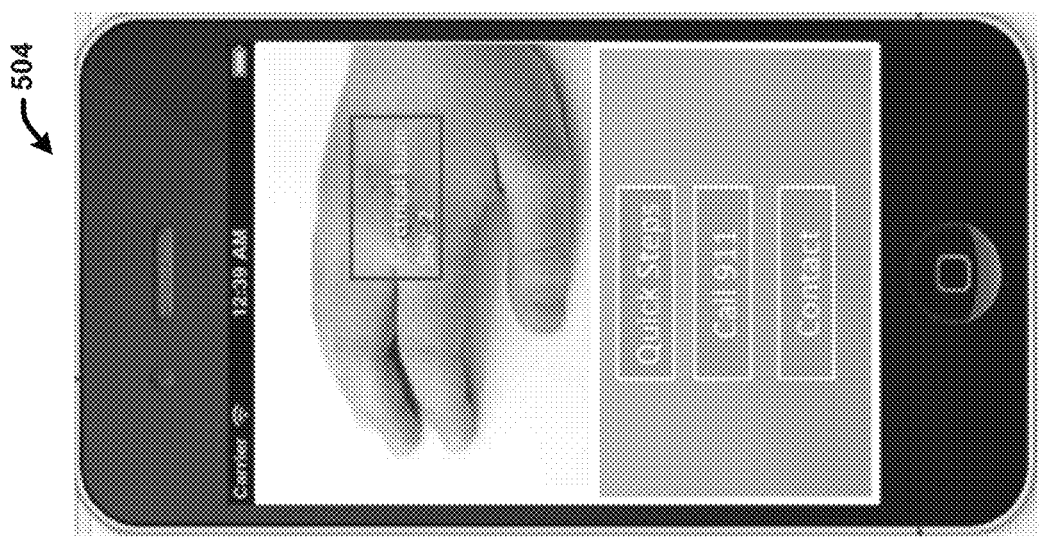
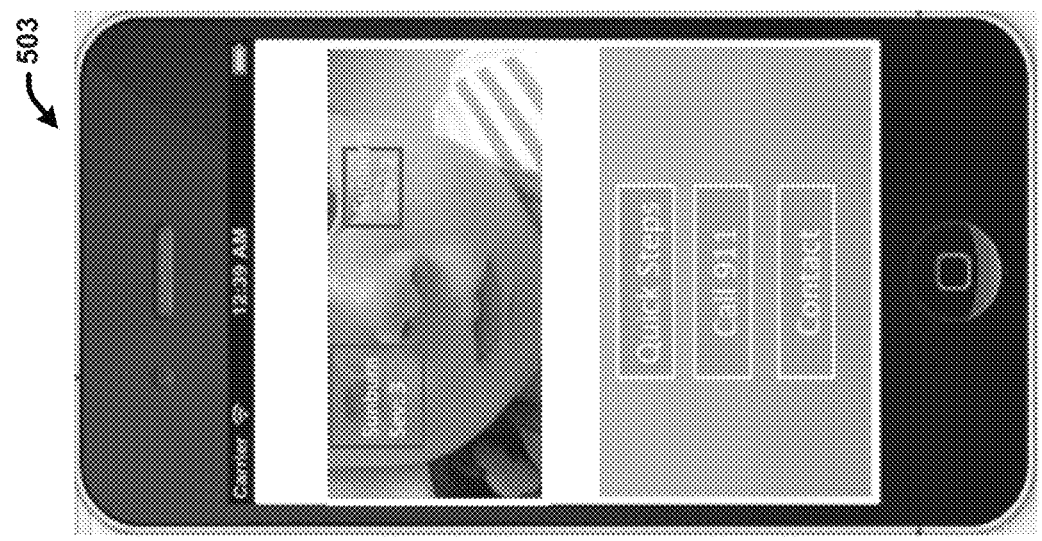
FIG. 5B

PROVIDING LIVE FIRST AID RESPONSE GUIDANCE USING A MACHINE LEARNING BASED COGNITIVE AID PLANNER

TECHNICAL FIELD

This application relates to computer-implemented techniques for providing live first aid response guidance using a machine learning-based cognitive aid planner.

SUMMARY

The following presents a summary to provide a basic understanding of one or more embodiments of the invention. This summary is not intended to identify key or critical elements or delineate any scope of the different embodiments or any scope of the claims. Its sole purpose is to present concepts in a simplified form as a prelude to the more detailed description that is presented later. In one or more embodiments described herein, systems, computer-implemented methods, apparatus and/or computer program products are presented that facilitate providing live first aid response guidance using a machine learning based cognitive aid planner.

According to an embodiment, a system is provided that comprises a memory that stores computer executable components, and a processor that executes the computer executable components stored in the memory. The computer executable components can comprise an injury classification component that classifies a type of an injury endured by a patient. The computer executable component can also comprise a risk evaluation component that employs one or more machine learning models to estimate a risk level associated with the injury based on the type of the injury a current context of the patient. In some implementations, the computer executable components can further comprise a model development component that trains and develops the one or more machine learning models based on historical incident information for previous patients that endured the type of the injury.

In various embodiments, the computer executable components can further comprise a treatment plan generation component that generates a treatment plan for treating the patient for the injury based on the type of the injury, the risk level, and the current context of the patient. In some implementations, the treatment plan generation component can employ one or more machine learning techniques to determine the treatment plan based on the type of injury, the risk level, the current context of the patient, and historical treatment information regarding actions and reactions associated with previous treatment of patients for the type of the injury. In other implementations, the risk evaluation component can further employ one or more machine learning techniques to determine one or more risk factors for the patient based on the type of the injury, the current context of patient and historical incident information for previous patients that endured the type of the injury, and the treatment plan generation component can further generate the treatment plan based on the one or more risk factors. The computer executable components can also comprise a guidance component that provides guidance to facilitate treating the patient for the injury based on the treatment plan. For example, the guidance can comprise visual or audible instruction rendered at a device associated with an entity identified to perform or facilitate the performance of the treatment plan for treating the patient for the injury.

In one or more embodiments, the computer executable components further comprise a behavior prediction component that predicts one or more reactive behaviors of the patient in response to the provision of treatment to the patient in accordance with the treatment plan. In some implementations of these embodiments, the treatment plan generation component can further generate the treatment plan based on the one or more reactive behaviors. In other implementations, the computer executable components can further comprise a behavior regulation component that determines one or more responsive actions to minimize harm attributed to the one or more reactive behaviors, and the treatment plan generation component can further incorporate the one or more responsive actions into the treatment plan.

The computer executable components can further comprise a monitoring component that monitors feedback information regarding the behavior of the patient and status of the injury over a period of time in association with treatment of the patient based on the treatment plan. In some implementations of these embodiments, the computer executable components can further comprise a plan updating component that determines one or more updates to the treatment plan based on the feedback information. The computer executable components can also comprise a plan evaluation component that evaluates the effectiveness of the treatment plan based on the feedback information and historical feedback information for patients that received treatment for the type of the injury in accordance with treatment plans that were similar to the treatment plan.

In one or more additional embodiments in which the system monitors feedback information regarding the behavior of the patient in association with treatment of the patient based on the treatment plan, the computer executable components can further comprise an affinity prediction component that estimates one or more affinities of the patient related to the treatment based on the feedback information. With these embodiments, the plan updating component can determine one or more updates to the treatment plan based on the one or more affinities. For example, in some implementations, the feedback information comprises interaction data captured via one or more sensors regarding interaction between the patient and one or more entities that provide or facilitate the treatment. In another example, the feedback information comprises reaction data captured via one or more sensors regarding one or more reactions of the patient to the treatment. In various implementations, the feedback information comprises sensory data captured via one or more sensors selected from a group consisting of: an eye tracking sensor, a motion tracking sensor, an acoustic sensor and an image sensor. In some implementations of these embodiments, the computer executable components can further comprise a plan updating component that determines one or more updates to the treatment plan based on real-time analysis of the feedback information.

In some embodiments, elements described in the disclosed systems can be embodied in different forms such as a computer-implemented method, a computer program product, or another form.

DESCRIPTION OF THE DRAWINGS

FIGS. 5A and 5B present example first aid guidance information as rendered at a mobile device in association with various example use cases of the disclosed system(s) for providing live first aid response guidance in accordance with one or more embodiments of the disclosed subject matter.

DETAILED DESCRIPTION

Figure 1:
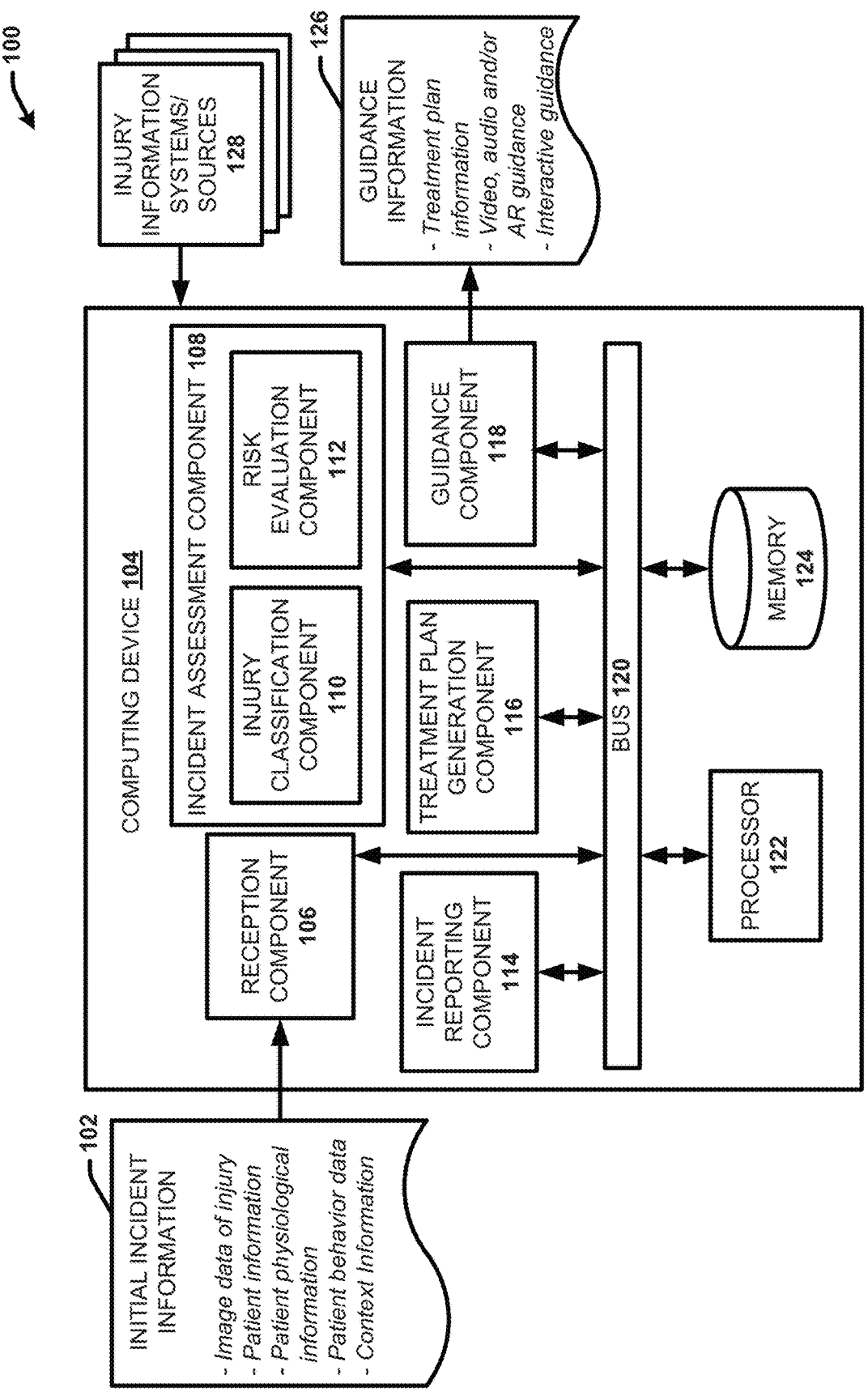
FIG. 1 illustrates a block diagram of an example, non-limiting system for providing live first aid response guidance using a machine learning based cognitive aid planner in accordance with one or more embodiments of the disclosed subject matter.

The following detailed description is merely illustrative and is not intended to limit embodiments and/or application or uses of embodiments. Furthermore, there is no intention to be bound by any expressed or implied information presented in the preceding Summary section or in the Detailed Description section.

The disclosed subject matter is directed to systems, computer-implemented methods, apparatus and/or computer program products that facilitate providing live first aid response guidance using a machine learning based cognitive aid planner. For example, in various embodiments, the cognitive aid planner can generate a cognitive aid plan for assisting one or more first responders to treat an injury or multiple injuries endured by a patient in non-clinical settings. In one or more embodiments, the disclosed techniques involve analyzing an injury or multiple injuries that appear on a patient's body based in part on image data captured of the injury or injuries. The disclosed techniques further employ one or more machine learning models/algorithms to estimate the risk and severity level of the injury based on the image data and/or one or more characteristics of the injury or the nature of the injury determined or inferred based on analysis of the image data. For example, characteristics of the injury can include the location of the injury, the coverage area of the injury, the width and depth of the injury, and the like. In some implementations, additional non-image data input (e.g., text, audio, sound waves, infrared, etc.) can also be received and processed to determine the nature and/or characteristics of the injury. The one or more machine learning models/algorithms can also estimate the risk and severity level of the injury based on characteristics of the patient (e.g., age, medical history, etc.) and the context of the injury or scenario in which the injury is being treated. The disclosed techniques further involve determining the cognitive states of the patient and/or the entities providing assistance or treatment to the patient in connection with the injury. Using information regarding the type of the injury, the estimated risk and severity level of the injury, the context of the injury and the cognitive states of the patient and entities involved in treatment, a machine learning based cognitive aid planner further generates a tailored cognitive aid plan (e.g., instructional treatment information, guidance, treatment actions, etc.) to assist the patient and/or entities performing in association with performing a first aid response. In some embodiments, techniques are also described to facilitate the first aid response process using voice, video and/or augmented reality (AR) applications and the generated cognitive aid plan.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Turning now to the drawings, FIG. 1 illustrates a block diagram of an example, non-limiting system 100 that facilitates providing live first aid response guidance using a machine learning based cognitive aid planner in accordance with one or more embodiments of the disclosed subject matter. Embodiments of systems described herein can include one or more machine-executable components embodied within one or more machines (e.g., embodied in one or more computer-readable storage media associated with one or more machines). Such components, when executed by the one or more machines (e.g., processors, computers, computing devices, virtual machines, etc.) can cause the one or more machines to perform the operations described.

For example, in the embodiment shown, system 100 includes a computing device 104 that includes various computer/machine-executable components, including reception component 106, incident assessment component 108, incident reporting component 114, treatment plan generation component 116 and guidance component 118. The computing device 104 can include or be operatively coupled to at least one memory 124 and at least one processor 122. The at least one memory 124 can further store executable instructions (e.g., the reception component 106, the incident assessment component 108, the incident reporting component 114, the treatment plan generation component 116, the guidance component 118 and additional components described herein) that when executed by the at least one processor 122, facilitate performance of operations defined by the executable instruction. The computing device 104 can further include a device bus 120 that communicatively couples the various components of the computing device 104 (e.g., the reception component 106, the incident assessment component 108, the incident reporting component 114, the treatment plan generation component 116, the guidance component 118, the processor 122 and the memory 124). Examples of said processor 122 and memory 124, as well as other suitable computer or computing-based elements, can be found with reference to FIG. 14, and can be used in connection with implementing one or more of the systems or components shown and described in connection with FIG. 1 or other figures disclosed herein.

In one or more embodiments, system 100 facilitates providing guidance (e.g., guidance information 126) to a patient or caregiver that facilitates guiding the patient or caregiver in association with treating the patient for an injury or multiple injuries currently endured by the patient. In various embodiments, the guidance can include live or real-time care instruction provided to the patient or caregiver at the time of initial reporting of the injury and/or over a period of time in which the patient continues to endure the injury. For example, in one or more embodiments, the guidance can include a treatment plan that identifies actions or steps to perform to facilitate treating the patient for the injury. In some implementations, the treatment plan can be or correspond to a cognitive first aid plan that facilitates providing initial aid to the patient to treat or alleviate the injury. For example, in one or more embodiments, system 100 facilitates receiving information from a patient or caregiver for the patient reporting an injury recently endured by the patient in accordance with daily life. For instance, in one example implementation, the patient can include a pediatric patient and the injury can include a rash on the pediatric patient's body just identified by the pediatric patient's mother. In accordance with this example, the pediatric patient's mother can employ system 100 to report the injury and receive immediate clinical guidance regarding how to respond. In another example implementation, the patient can be an older pediatric patient or adult cable of reporting an injury they endured themselves. With this example implementation, using system 100, a person can report an injury that just or recently occurred to them, such as a gash on the person's knee as a result of slip and fall accident, and receive immediate guidance regarding how to respond.

With these example implementations in mind, the computing device 104 can include reception component 106 to receive initial incident information 102 reporting an injury or injuries endured by a patient. The initial incident information 102 can include a variety of rich information that facilitates automatically classifying a type and severity level and determining how to respond to the injury based on the specific type of injury, the severity level, and various additional factors related to the patient and the current context of the patient. In one or more embodiments, the initial incident information 102 can include image data of the injury or injuries, including photographs and/or video of the injury or injuries. For example, in some implementations, in association with reporting an injury that can be visually observed on the patient's body (e.g., a rash, a gash, etc., as opposed to an physiological illness), the patient or a caregiver of the patient (e.g., another person or entity currently with the patient) can use a camera to capture and provide one or more images and/or video of the injury to the reception component 106. In some implementations as described infra with reference to FIG. 4, the computing device 104 itself can include a mobile device including the camera. With these implementations, using the camera of the computing device 104, the patient or caregiver of the patient can capture and provide the image data (e.g., still photographs and/or video) to the reception component 106 in association with reporting the injury.

The initial incident information 102 can also include information identifying the patient and/or providing individual characteristics of the patient that can influence determining the type of the injury, the severity of the injury and/or how to respond to the injury. For example, certain injuries, types of injuries, severity level of the injuries and/or manner for treating the injuries can vary based on specific characteristics of the patient, including, (but not limited to): demographics such as age, geographic location, etc., body measurements (e.g., height and weight), medical history, medications taken, allergies and the like. In some implementations, the various individual characteristics of a patient can be collectively referred to as patient profile characteristics. For instance, there are several injuries that are commonly endured by pediatric patient, including but not limited to: burns (e.g., sun burns, electrical burns, burns caused by flames from stoves, touching a hot surface, touching hot liquid, etc.), ingesting harmful substances or gases, ingesting excessive quantities of medications/vitamins, etc., drowning, falls, choking, and the like. In some implementations, the initial incident information 102 can include information identifying the patient (e.g., by name or another unique identification measure) that can be used to determine the individual characteristics of the patient. For example, in one or more implementations, based on reception of information identifying the patient, the reception component 106 can access one or more data sources and/or system including information about the patient, such as network accessible electronic health record (EHR) systems, or the like. The reception component 106 can further retrieve the relevant patient information (e.g., age, body measurements, medical history, medications taken, etc.) from these types of data sources and/or systems.

The initial incident information 102 can also include measured physiological parameters related to the patient's current physiological state or condition. For example, the measured physiological parameters can include vital sign parameters and various other physiological parameters (e.g., heart rate, blood pressure, SpO2, respiratory rate, temperature, hypertension, hydration level, glucose level, cortisol level, potassium level, etc.). In some implementations, the physiological parameters can be received by the reception component 106 directly from one or more medical monitoring device and configured to read and report monitored physiological parameters. For example, the medical monitoring devices can include a device worn by, within (e.g., an implantable medical device (IMD)), and/or physically connected to the patient and configured to capture and/or monitor physiological information (e.g., physiological parameters) that can be sent to or otherwise received by the reception component 106 in real-time or substantially real-time. In other embodiments, the medical monitoring devices can include a device that is operated by another person other than the patient (e.g., a caregiver).

The initial incident information 102 can also include patient behavior data regarding the behavior of the patient as observed by a caregiver and/or the patient. For example, the patient behavior data can include information regarding how the patient is currently feeling and/or behaving at the time of initial reporting of the incident. For instance, the behavior data can indicate whether the patient is conscious or unconscious, coherent or incoherent, crying, screaming, sleeping, breathing, itching, kicking, etc. In another example, the patient behavior data can include information regarding a physical position of the patient and/or physical capabilities of the patient (e.g., mobility, range of motion, etc.) of the patient. For instance, the behavior data can indicate if the patient is lying down, sitting, standing, walking, etc. In another example, the behavior data can indicate whether the patient is capable of moving, sitting standing, putting pressure on a particular body part (e.g., standing on a foot that is injured), moving a particular body part with a certain range of motion (e.g., lifting arms above head). The behavior data can also report symptoms and sensations felt by the patient (e.g., in implementation in which the patient is capable of communicating this information), such as information regarding pain location, pain level, dizziness, feeling sick one's stomach, headache, tingling, loss of feeling or sensation in a particular body part, itching, burning, etc.

The initial incident information 102 can also include context information regarding the context of the injury and/or the patient. For example, in some embodiments, the context information can include information describing the incident or scenario in which the injury was received and/or observed by the patient and/or a caregiver of the patient. In this regard, the incident description can include information describing essentially what happened to the extent known. For example, the incident description can include a description of the accident that occurred which resulted in causing the injury. In another example, the incident description can include a description of the scenario or context in which the patient or caregiver of the patient first observed the injury. For example, in a scenario in which a patient received a physical injury but the patient is unable to communicate what happened to cause the injury, the incident description can include information identifying the events or scenario the led up to the injury, when and where the injury was initially observed, the behavior of the patient at the time the injury was initially observed, relevant behavior or activity of the patient prior to observing the injury (e.g., the patient was playing in the woods before the injury was observed), the condition of the patient at the time the injury was observed, and the like. In other implementations in which the injury includes a physiological illness or condition, such as a disease or sickness, the incident description can include information identifying the signs and symptoms of the patient, the behavior of the patient at the time in which the illness or condition is reported and/or over a period of time from the assumed onset of the illness or condition and leading up to the time of reporting of the condition or illness (e.g., signs and symptoms over the past hour, the past 24 hours, the past few days, etc.).

The context information can also include information identifying a current time/day and/or the time/day when the injury occurred or was observed, location information identifying a current location of the patient, current and forecasted weather, a current mobility state of the patient (e.g., walking, driving, riding as a passenger, unable to walk or stand), and directional information regarding where a patient is going in the context in which the patient is traveling. In some implementations, the context information can also identify the distance of a patient relative to one or more healthcare facilities or clinics. The context information can also include information regarding a current environment of the patient. In this regard, the environment information can include additional descriptive characteristics of the current location of the patient. For example, the environment information can indicate whether the patient is at home, at work, indoors, outdoors, at a park, in a parked vehicle, etc. In another example, the environment information can describe current events or activities associated with the current location (e.g., a festival, a concert, etc.).

The context information can also include information identifying or indicating who is with the patient and/or if the patient is alone, who is assisting the patient, and/or who is available to assist the patient. In some implementations in which the patient has assistance by one or more caregivers (e.g., a friend, family member, good Samaritan, etc.), the context information can also include information about the one or more caregivers. For example, the information about the one or more caregivers can include information regarding a caregiver's experience in association with providing medical care for the type of injury endured by the patient and/or providing medical care in general. The information about the one or more caregivers can also include information regarding the physical and mental capabilities of the caregiver in association providing care for the patient (e.g., whether the caregiver can administer medication, whether the caregiver can perform a particular medical procedure, whether the caregiver can transport the patient to a healthcare facility or move the patient, as some mental states might preclude the caregiver's ability to render assistance, etc.). The information about the one or more caregivers can also include information regarding their current mental state (e.g., scared, stressed, distressed, anxious, intoxicated, etc.). In some embodiments, the context information can also include information regarding (non-human) resources available to treat the patient, such as information regarding available supplies, equipment and the like.

The incident reporting component 114 can facilitate gathering the initial incident information 102 in association with initial reporting an injury. In some embodiments as discussed in greater detail infra with reference to FIG. 7, the incident reporting component 114 can also facilitate continued gathering of such information over a period of time after initial reporting of the injury (e.g., over a course of treatment of the injury or a period of monitoring the patient following initial reporting of the injury). In this regard, in one or more embodiments, the incident reporting component 114 can provide an electronic reporting function that allows an entity (e.g., the patient, a caregiver, a hospital, Emergency Medical Technician (EMT), or another suitable entity) to provide input comprising or regarding one or more components of the initial incident information 102 to a device in association with a request to receive guidance for responding to an injury. For example, in one implementation, the device at which the input is entered by the reporting entity can be the computing device 104. In other implementations, the device can include a separate communication device accessible to the reporting entity that is communicatively coupled to the computing device 104 (e.g., a mobile device operated by the reporting entity, such as a smartphone). In either of these implementations, using one or more input mechanisms/devices (e.g., a keypad, a touchscreen, a camera, an audio recording device, an acoustic sensor, etc.) of the computing device 104 or the separate communication device, the reporting entity can generate an incident report message by entering, attaching or otherwise providing one or more components of the initial incident information 102 (e.g., image data of the injury, patient physiological information, patient behavior data, context information, etc.) to the device (e.g., the computing device 104 or a separate communication device). The device can further facilitate sending or otherwise providing the incident report request message to the reception component 106. In some implementations, the incident reporting component 114 can provide a reporting application that facilitates entering the initial incident information, formatting the incident report message, and sending or otherwise providing the incident report message to the reception component 106. In this regard, upon reception of input requesting to send the incident report message, the incident reporting component 114 can provide the initial incident information to the reception component 106.

In some embodiments, the incident reporting component 114 can employ one or more speech to text technologies for converting spoken initial incident report information 102 to text. With these embodiments, the patient or a caregiver for the patient reporting the injury/incident can describe the incident, the injury, the patient, the patient physiological information, the patient behavior data, the context information and the like using natural language and a microphone and/or recording device. The incident reporting component 114 can further convert the spoken input description into text in association with providing the initial incident information to the reception component 106. In some embodiments, the incident reporting component 114 can also employ one or more natural language processing (NLP) functions to identify and extract defined terms and phrase included in the user provided initial incident information (e.g., either as text or speech to text). The incident reporting component 114 can further convert the natural language into a defined format including the terms and/or phrases formatted in a defined computer readable format capable of being efficiently processed by the incident assessment component 108 and/or the treatment plan generation component 116.

In other embodiments, the incident reporting component 114 can provide the patient, the caregiver, or another suitable entity submitting the incident report with one or more prompts including defined questions regarding the types of initial incident information desired. For example, in association with initiating a request to report an injury using system 100 to receive guidance for responding to the injury, the incident reporting component 114 can guide the user through a series of automated questions, the answers to which provide the relevant initial incident information desired for processing by the incident assessment component 108, and/or the treatment plan generation component 116. For example, in one implementation, in association with initiating reporting an incident/injury, the incident reporting component 114 can begin by asking the user if the user or another person is in an emergency situation and initiate a call to emergency services as appropriate. The incident reporting component 114 can further ask the user if they are reporting an injury for themselves or another person (e.g., their pediatric patient, their friend/or family member, or another person not yet recognized by the system). In some embodiments, the system 100 can retain information for respective users regarding who they are and other individuals that they care for. The incident reporting component 114 can further tailor the questions to the respective users. For example, assuming system 100 is employed by a known parent named "Donna" who has three known pediatric patient, "Jake, "Jane," and "John," in association with initiating an incident report using the system 100, the incident reporting component can recognize Donna as the user (e.g., based on a device identifier associated with Donna used to initiate the incident report, based on usage of a registered account set up for Donna with system 100, etc.). Based on recognizing Donna as the user initiating the incident report, the incident reporting component 114 can generate one or more prompts tailored to Donna based on known or learned information about Donna or her pediatric patient. In accordance with this example, the initial prompt could include a question in accordance with the following: "Hi Donna, are you injured? (yes, or no)," and allow the user (Donna) to select yes or no. In response to selection of the option "no," the next prompt could then ask, "Is Jake, Jane or John injured, or someone else?" and provides options to select one or more of the identified individuals or options. Further, in implementations in which Donna has previously provided information about herself and/or her pediatric patient regarding their age, medical history and the like, the system can automatically access and input this information into the incident report message if relevant. In another embodiment, the system can update the stored information automatically (e.g. the pediatric patient's ages, physical condition, primary care provider, etc.).

In some embodiments in which the incident reporting component 114 facilitates receiving one or more components of the initial incident information 102 through a series of questions/prompts, the incident reporting component 114 can further employ one or more machine learning and/or artificial intelligence (AI) techniques to tailor the prompts/questions to the user based on the specific responses/information provided by the user. For example, if the user provides information indicating that the patient (e.g., themselves or another person) has endured a particular type of injury, the incident reporting component 114 can tailor the questions/prompts based on the type of injury. Likewise, the incident reporting component 114 can tailor the questions/prompts based on received information regarding the incident description, the patient information, the patient physiological information, the patient behavior, the context of the incident, and the like.

In various additional embodiments, the incident reporting component 114 can automatically receive and/or determine one or more components of the initial incident information 102 (e.g., in addition to and/or alternative to receiving user reported initial incident information). For example, in some embodiments, the incident reporting component 114 can receive patient physiological information from one or more medical devices (e.g., IMD, biofeedback devices, and other medical monitoring devices) associated with the patient, if available. The incident reporting component 114 can also determine information regarding a patient's medical history by accessing the medical history information in one or more EHR systems using information identifying the patient (e.g., determined based on user input, determined based on the device/account used to generate the incident report, determined using facial recognition software, etc.). In other implementations, the patient can wear (e.g., in clothing or accessories) otherwise be physically coupled to one or more motion sensors (e.g., included in a device worn or held by the patient). With these embodiments, the incident reporting component 114 can automatically receive and process motion/movement information to determine certain behavior data of the patient, such as information regarding a physical position of the patient, movement of the patient, range of motion of the patient, a mobility state of the patient, and the like. In one embodiment the sensor can detect and report if a patient has fallen by the presence of sudden acceleration. The incident reporting component 114 can also automatically receive audio/sound associated with the patient and the patient's environment captured via one or more acoustic sensors. The incident reporting component 114 can further employ one or more audio analysis technologies to process the audio/sound to determine various types of information regarding the patient, the context of the incident, and the like. The incident reporting component 114 can further automatically receive and/or determine information regarding the location of the patient using various location detection techniques. For example, in implementations in which the patient is associated with a device including a global position system (GPS) application, the incident reporting component 114 can automatically receive GPS information from the device in association with an incident report. The incident reporting component 114 can also track movement and/or change in location of the patient using the GPS information. The incident reporting component 114 can also determine information regarding other entities located with or near the patient based on tracking the locations of mobile devices associated with those entities. Still in other embodiments in which the incident reporting component 114 receives image data of the patient/injury, the incident reporting component 114 can process the image data to determine information regarding the injury, the patient, the patient's environment, other individuals with or near the patient and the like using image processing analytic software (e.g., facial recognition software, object recognition software, etc.) that employ various classification techniques (e.g., machine learning based classification techniques, statistical classification techniques, etc.). The incident reporting component 114 can also analyze video data captured of the patient to determine patient behavior information.

The incident assessment component 108 provides for evaluating the initial incident information 102 to assess the reported injury or injuries in view of the various factors associated with the patient and the context of the injury included in and/or determined based on the initial incident information 102. In the embodiment shown the incident assessment component 108 can include injury classification component 110 and risk evaluation component 112.

In one or more embodiments, the injury classification component 110 can evaluate the initial incident information 102 to classify a type of the injury and/or determine one or more characteristics of the injury. In some implementations, the types of injuries can include essentially all known types of medical injuries (e.g., including different types of medical conditions, illnesses, diseases, etc.). In other implementations, the types of injuries capable of being classified by the injury classification component 110 can be specific to a particular patient group (e.g., common types of pediatric injuries, common types of pediatric patient injuries, common types of adult injuries), activity (e.g., exercise injuries, vehicular injuries, etc.), geographic region, or another suitable aggregation factor. The characteristics of an injury can include descriptive features or parameters of an injury. For example, with respect to a visible injury shown in received image data, the characteristics of the injury can include (but are not limited to), the location of the injury, the coverage area of the injury, the size and dimensions of the injury (e.g., width and depth), a hue of the injury, defined clinical attributes of the injury, and the like.

In some embodiments, the injury classification component 110 can also determine or infer a severity level of the injury of an injury based on the type and/or characteristics of the injury. In accordance with these embodiments, the severity level of an injury can reflect different degrees of severity of an injury in isolation (e.g., without considering patient parameters and/or contextual parameters). For example, the severity level of a cut can reflect the size and depth of the cut and the method for which the cut occurred (glass, knife, jagged rusty steel, etc.). In another example, the severity level of a sprain can reflect the degree of pain and swelling associated with the sprain area. In some implementations, in association with classifying a type and/or severity level of an injury, the injury classification component 110 can also determine information regarding the probability of a particular type and/or state of an injury. For example, the injury classification component 110 can determine the probability that an injury to a patient's wrist involves a sprain or a broken bone. In another example, the injury classification component 110 can determine the probability that a rash is a result of a particular pathogen, the result of a contagious disease, or an allergic reaction to, for instance, a bee sting. In another example, the injury classification component 110 can determine the probability that a cut requires stitches or not.

The injury classification component 110 can employ various techniques to determine the type of an injury (or injuries), one or more characteristics of the injury and/or severity level of the injury based on the type of initial incident information 102 provided. In various embodiments, the injury classification component 110 can determine the injury type, characteristics, and/or severity level using one or more machine learning classification models configured evaluate injury based on one or more input parameters included in the initial incident information 102. The one or more machine learning models can be stored in memory 124, provided by one or more injury information systems/sources 128 and/or otherwise accessible to the injury classification component 110. For example, in some implementations in which the initial incident information 102 includes image data of the injury (e.g., photographs and/or video), the injury classification component 110 can employ one or more machine learning models (e.g., neural network models, deep neural network (DNN) models, convolutional neural network (CNN) models, etc.) configured to process the image data to determine an injury type, injury characteristics, and/or severity level of the injury based on the image data. For instance, in some embodiments, the injury classification component 110 can employ one or more first image classification models/algorithms configured to process the image data to determine a type of the injury (e.g., sun burn, electrical burn, burn caused by flames, etc.). For example, the one or more first image classification models/algorithms can include injury models trained on historical image data of injuries representing different types of injuries with different characteristics. In some embodiments, the one or more first image classification models can be configured to identify and/or determine characteristics of an injury (e.g., regarding location, size, dimensions, appearance, etc.) based on analysis of the image data. The injury classification component 110 can also evaluate non-image-based data (e.g., text, infrared measurements, sound wave measurements, etc.) to determine one or more characteristics and/or a type of an injury using machine learning models trained on historical injury data. The injury classification component 110 can also employ one or more second image classification models/algorithms configured to process the image data to determine a severity level of the injury using a defined valuation model (e.g., on a scale from 1 to 5 wherein 1 indicates the lowest level of severity and 5 indicates the highest level of severity). The model can be trained based on a database of images of previous injuries of same or similar types and/or with same or similar characteristics (e.g., location, size, coverage, dimensions, etc.).

One suitable model/algorithm capable of classifying injury type and/or severity from video data can use a time information fusion-based approach. The approach considers a video as a bag of fixed-sized segments and extends the connectivity of the network in the time dimension to learn spatio-temporal features for classification based on three connectivity patterns: early fusion, slow fusion, and late fusion. The CNN model is trained using a multiresolution CNN architecture. Another suitable machine learning model capable of classifying injury type and/or severity from images also employ an architecture based on CNN.

The risk evaluation component 112 can further evaluate the initial incident information 102 to determine risk information for the injury/incident that indicates one or more risks factors associated with the injury and/or a level of risk associated with the injury. The risk factors and/or the level of risk can be based not only on the type of the injury, the characteristics of the injury and/or the severity of the injury, but also the various conditional factors associated with the injury, the patient and the context of the incident. In this regard, in various embodiments, the severity level of an injury can be independent of the patient and/or context of the injury. For example, in some embodiments, the severity level of a cut can be based on the size and depth of the cut and where it occurs on the body. For instance, assume a pediatric patient is cut on a foot by a sharp tree branch while located at a campground far from a medical facility and/or medical resources for treating the cut. Now assume an experienced nurse cuts herself on the hand accidentally with a knife while cooking at home. According to this example, if the cut on the pediatric patient was the same in size and depth as the cut on the nurse, the respective cuts would be classified with the same severity level. However, because the pediatric patient is located far from medical resources and experienced aid, the pediatric patient's injury would be considered higher risk relative to the nurse's injury. In addition, because the pediatric patient is located at a campground and was cut by a tree branch as opposed to a knife, the pediatric patient's injury could be associated with additional risk factors relative to the nurse's injury, such as higher chance of infection, possible allergic reaction to the tree branch, etc. Further, the location of the pediatric patient's cut on the body could be associated with additional risk factors based on the location of the cut and known behavior of the pediatric patient. For example, additional pressure on the cut as a result of walking or standing could prevent the cut from healing or exacerbate the injury. Because it can be difficult to keep the pediatric patient from walking, playing or otherwise putting additional pressure on the cut, the pediatric patient's cut could be associated with a higher risk level relative to the nurse's cut.

In this regard, the risk evaluation component 112 can further characterize the risks and/or a risk level associated with the patient and the injury based not only on the type of the injury, one or more characteristics of the injury and/or a severity level of the injury, but also various additional conditional factors included in and/or determined from the initial incident information 102 regarding the patient, the injury (e.g., a specific body location of the injury) and the context of the incident. Further, in implementations in which the patient has multiple injuries (e.g., two or more), the risk evaluation component 112 can determine one or more risk factors and/or a risk level associated with the patient based on the combined risk attributed to the injuries. For example, the risk evaluation component 112 can determine one or more risk factors and/or a risk level associated with the patient/incident based on the number of injuries, the types and locations of the injuries, characteristics of the injuries, the severity levels of the injuries and the various conditional factors associated with the patient and the context of the injuries. The risk evaluation component 112 can further evaluate the risk based on known or learned interactions and/or interdependencies attributed to the combination of the injuries (e.g., including what treatments can and cannot be performed based on, for example, the combination of the injuries, based on one injury exacerbating another, etc.).

In various embodiments, the risk evaluation component 112 can employ one or more machine learning models/algorithms trained, based on historical incident information for previous patients that endured the type of injury and/or the type of injury with same or similar characteristics (e.g., location, coverage, size, dimensions, clinical attributes, appearance, etc.) to determine one or more risk factors and/or a risk level associated with an injury/incident.

Figure 2:
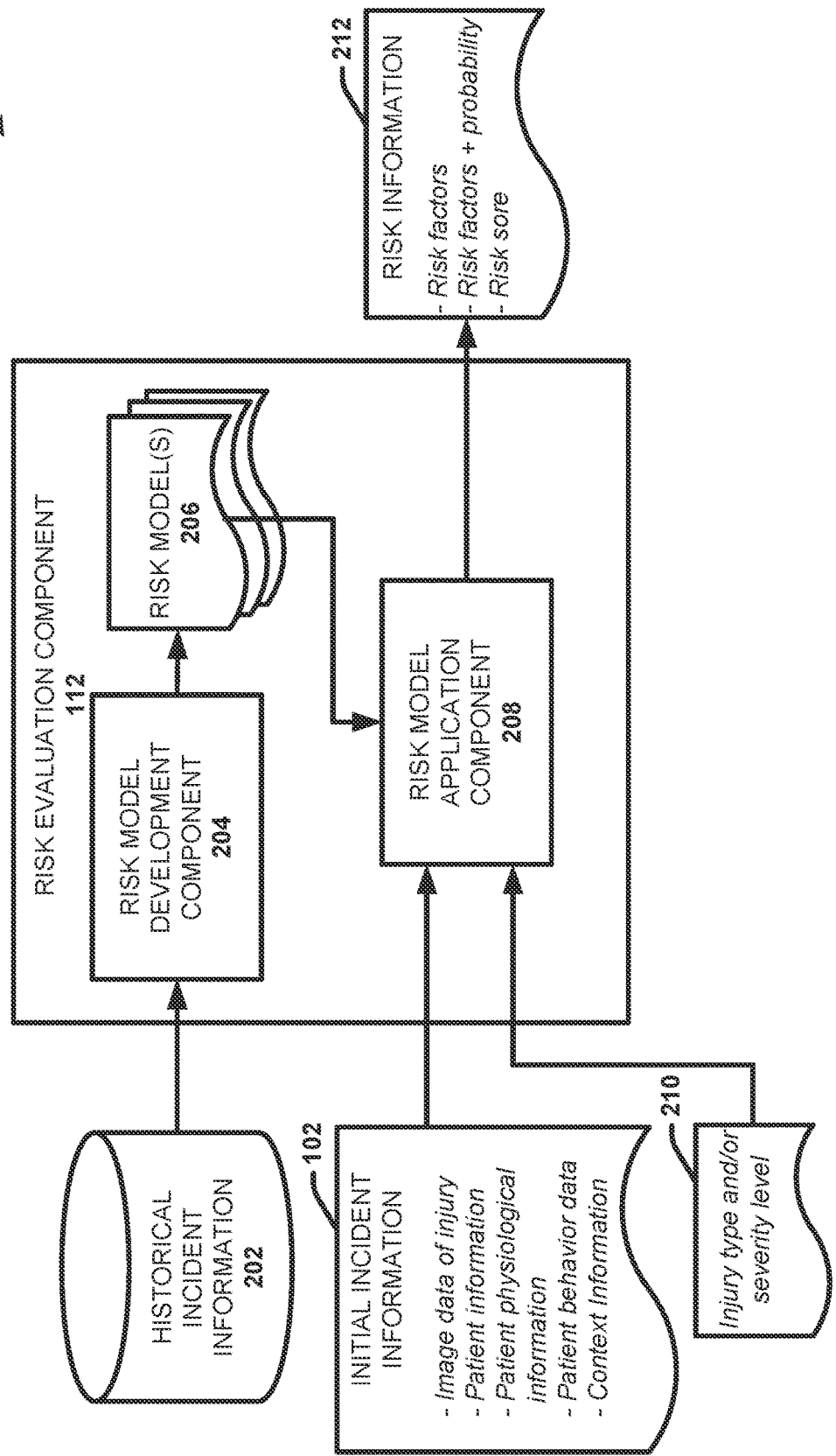
FIG. 2 presents an example, non-limiting system for training and applying one or more machine learning models to predict risks associated with injuries that occur under various conditions in accordance with one or more embodiments of the disclosed subject matter.

For example, FIG. 2 presents an example, non-limiting system 200 for training and applying one or more machine learning models to predict risks associated with injuries that occur under various conditions in accordance with one or more embodiments of the disclosed subject matter. In various embodiments, system 100 can include system 200, or vice versa. Repetitive description of like elements employed in other embodiments described herein is omitted for sake of brevity.

System 200 includes the risk evaluation component 112 as well as historical incident information 202. In the embodiment shown, the risk evaluation component 112 includes a risk model development component 204, one or more risk models 206 and a risk model application component 208. In some embodiments, the risk model development component 204 can train and develop the one or more risk models 206 based on the historical incident information 202. The risk model application component 208 can further apply the one or more risk models 206 (e.g., after they are developed and trained) to the initial incident information 102 and information 210 regarding the injury classification type, characteristics of the injury, and/or severity level (e.g., as determined by the injury classification component 110) to determine risk information 212 for the injury/incident. The risk information 212 generated as a result of application one or more risk models 206 can include one or more identified risk factors, probability information indicating an estimated probability of occurrence of the one or more risk factors, and/or a risk score.

For example, in some embodiments, the one or more risk models 206 can include models configured to determine one or more risk factors for an injury/incident based on the type of injury, one or more characteristics of the injury, and/or severity level of the injury and various defined parameters regarding the injury, the patient, the age of the patient, and the context of the injury included in the initial incident information 102. For example, in some implementations, the risk factors can include known complications or issues and/or undesired patient reactions (e.g., infection, spreading of rash, allergic reaction, development of a secondary illness or condition, etc.). In other implementations, the risk factors can include undesired patient behaviors, such as pulling off bandages, scratching, failing to rest, failing to take medication, failing to eat or drink, performing movements or actions that exacerbate an injury, etc.). The risk factors can also include undesired or unfavorable response/reaction or behaviors of the first responder or entity assisting the patient (e.g., a first responder may attempt to move the patient however this might result in complication X). In some implementations, the risk factors can also include a time component. For example, in addition to identifying a complication or reaction, a risk factor can be associated with a time component indicating a time when then the expected complication will arise (e.g., within the next hour the patient may develop a secondary illness or conditions Y, the rash may spread to the face over the next 24 hours, the patient might lose a pint of blood within the next hour if the bleeding doesn't stop, etc.).

In other embodiments, in addition to determining one or more risk factors associated with an injury/incident, the one or more risk models 206 can also include models to configured to determine the likelihood of occurrence of the risk factors. For example, the one or more risk models 206 can be configured to determine or infer information identifying an estimated probability of occurrence of a specific complication, undesired patient reaction, undesired patient behavior and the like. In another example, the one or more risk models 206 can be configured to determine or infer an estimated probability of a particular complication arising if a certain treatment is performed or not performed. For example, the one or more risk models 206 can be configured to determine or infer the probability of infection or occurrence of a secondary illness or condition if stitches are not received, if a particular medication is administered, if a particular medical procedure is performed, or not, etc.

In one or more additional embodiments, the one or more risk models 206 can include models configured to generate a risk score for an injury/incident or combination of injuries associated with a single incident. For example, in some embodiments, the risk score can reflect the type of injury, the severity of the injury, the complications/reactions/undesired behaviors associated with the injury/incident and the probability of occurrence of the complications/reactions/undesired behaviors. In this regard, the risk score can reflect the totality of risk associated with the incident considering not only the type and severity level of an injury but the various contextual parameters associated with the injury, the patient and incident. For example, in some implementations the risk score for a particular type of injury can be based on a plurality of parameters including but not limited to: the severity of the injury, the location of the injury on the body (e.g., a specific type of rash near the patients eye could be attributed to a higher risk relative to the rash being located on the patient's arm), other visible attributes/characteristics of the injury (e.g., coverage area, dimensions, hue, etc.), the age of the patient, known allergies of the patient, known additional medical conditions/illnesses' of the patient, values of vital signs determined for the patient, pain levels expressed by the patient, physical behaviors of the patient (e.g., cannot get up, cannot put pressure on the injury, etc.), a location of the patient, availability of an entity to provide first aid assistance, an experience level of the entity identified to provide a first aid response or otherwise treat the patient, known complications/reactions/undesired behaviors, probability of occurrence of the complications/reactions/undesired behaviors (e.g., based on the specific patient, severity level and context), popularity of the injury type, time of day, and the like.

In some embodiments, the one or more risk models 206 can include a different model specifically configured to evaluate the risk factors for a particular type of injury. For example, the one or more risk models 206 can include a risk model configured to determine risk factors for a chemical burn and a different risk model configured to determine risk factors for an incident involving ingestion of substances or gases. With these embodiments, the risk model application component 208 can select and apply the appropriate risk model (or risk models) from amongst the different risk models 206 that is tailored to the reported injury based on the determined type of the injury. Further, in some implementations, for each (or in some implementations one or more) different type of injury, the one or more risk models 206 can include a different model specifically configured to evaluate the probability of occurrence of a particular complication, reaction, undesired behavior and the like for a particular type of injury. For instance, the probability of infection might differ for a chemical burn compared to a shallow cut.

As noted above, in some embodiments the risk model development component 204 can develop and train the one or more risk models 206 based on the historical incident information 202 using one or more machine learning techniques. For example, in some implementations, the historical incident information 202 can include the same type of information included in the initial incident information 102 as previously received and recorded for previous patients for various different types of injuries in different contexts. In this regard, the historical incident information 202 can identify, as grouped by injury type, the number of recorded incidents of the injury, characteristics of the injury (e.g., regarding location, dimensions, appearance, hue, coverage, nature of the injury, etc.), information about the patients, information about the injury (e.g., body location, severity, whether a sprain or bone break was determined, etc.), information about the tracked physiological parameters, information describing the patient's behavior and contextual information regarding the context of the injury (e.g., from onset or initial reporting to recovery or end of treatment). In some implementations, the historical incident information 202 can further include information regarding the course of treatment that was provided or not (e.g., actions performed, medications administered, medical procedures performed, etc.), patient reactions, complication, issues, and behaviors observed. The historical incident information 202 can also include information regarding the final outcome of the treatment of the patient for the injury or injuries (e.g., taken to the emergency room, recovered at home within 24 hours, cut turned into an infection, etc.).

In this regard, using one or more machine learning techniques, for each (or in some implementations one or more) injury classification type, the risk model development component 204 can evaluate the historical incident information 202 to learn correlations and patterns between different risk factors and/or risk levels and various parameters associated with the type of injury, characteristics of the injury (e.g., regarding location, coverage, dimensions, appearance, hue, etc.), the patient, and the context of the injury. For example, the risk model development component 204 can learn correlations between risk factors and/or a risk level associated with an injury/incident and parameters such as patient age, patient condition, first responder experience level, previous/current injury status, popularity of the injury type, and the like. The risk model development component 204 can further identify and extract feature vectors corresponding to the relevant parameters based on the learned correlations correlation.

With reference again to FIG. 1, the treatment plan generation component 116 can further generate a treatment plan for responding to the injury/incident based on the initial incident information 102, the type and/or severity of the injury reported, and the determined risk information (e.g., identifying risk factors, probability of occurrence of the risk factors, and/or a risk score for the injury/incident as a whole). For example, the treatment plan can be or correspond to a cognitive aid plan for providing a first aid response to the patient. In this regard, the treatment plan can identify a course of care for following, an ordered list of actions to perform (or not perform), medications to administer and the like. The treatment plan generation component 116 can further tailor the treatment plan based not only on the type of injury and/or a severity level of the injury but the determined risk information and the specific characteristics associated with the patient and the context of the incident. For example, the treatment plan generation component 116 can determine one or more actions for performing or not performing by the first aid responder (e.g., which could be the patient or another person assisting the patient) to perform that will minimize or reduce the risk and/or likelihood of occurrence of the determined risk factors. The treatment plan generation component 116 can also determine one or more actions for performing or not performing based on the location of the injury, the age of the patient, the medical history of the patient, the behavior of the patient, the location of the incident, the time of day, the weather, the available resources, the experience level of the first responder, and various other contextual parameters.

In various embodiments, the treatment plan generation component 116 can also employ AI and/or one or more machine learning techniques to determine a treatment plan for a particular injury/incident based on evaluation of known or historically performed treatment plans or treatment actions for similar patients with similar injuries under similar contexts.

Figure 3:
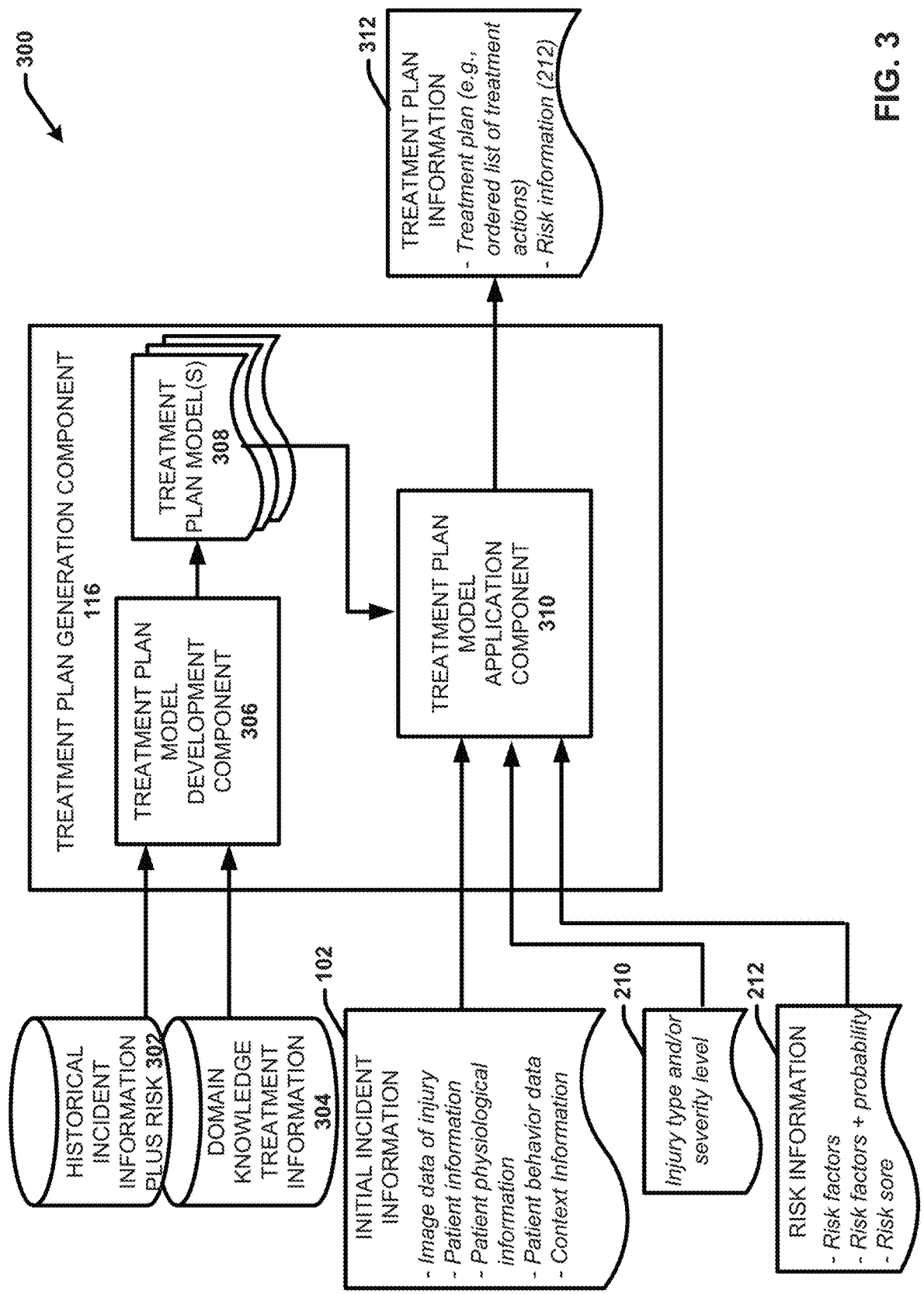
FIG. 3 presents an example, non-limiting system for training and applying one or more machine learning models to determine cognitive plans for treating injuries that occur under various conditions in accordance with one or more embodiments of the disclosed subject matter.

FIG. 3 presents an example, non-limiting system for training and applying one or more machine learning models to determine cognitive plans for treating injuries that occur under various conditions in accordance with one or more embodiments of the disclosed subject matter. In various embodiments, system 100 can include system 300, or vice versa. Repetitive description of like elements employed in other embodiments described herein is omitted for sake of brevity.

System 300 includes the treatment plan generation component 116 as well as historical incident information plus risk 302 and domain knowledge treatment information plus risk 304. The historical incident information plus risk 302 can comprise same or similar information as the historical incident information 202 with the addition of determined risk information (e.g., risk factors, probability of occurrence of the risk factors, and/or a risk score) for each historical recorded injury/incident. In various embodiments, the risk information included in the historical incident information plus risk 302 database was determined by the risk evaluation component 112 using the techniques described herein. In this regard, the historical incident information plus risk 302 database can include information identifying previously reported or observed incidents of various different types of injuries endured by a plurality of patients. For each (or in some implementations one or more) type of injury, the historical incident information plus risk 302 database can further include information identifying the severity level of the injury, the determined risk information, characteristics of the patient, context information associated with the incident, and treatment information regarding the treatment processes and/or actions that were performed (or not), and the outcomes (e.g., patient reactions) of the respective treatment actions and/or processes as a whole.

The domain knowledge treatment information 304 can include various types of published documents, articles, information from professionals and describing clinically known treatment actions or processes that are recommended for treating respective types of injuries. For example, the domain knowledge treatment information 304 can include information provided by experts (e.g., physicians, clinicians, nurses, etc.), in the field identifying known actions to perform (best known practices) and/or not to perform in association with treating a patient for a particular type of injury and/or combination of injuries. These treatment plan actions can be associated with a standard operating procedure of a particular medical institution or generally accepted by a community of peers as an appropriate or preferred process for treating a particular type of the injury.

In various embodiments, using the historical incident information and risk 302 information and/or the domain knowledge treatment information 304 and one or more machine learning techniques, the treatment plan model development component 306 can evaluate different treatment processes and/or actions were performed and/or are recommended for performance to treat a particular type of injury. In association with evaluating the different treatment plans/actions, the treatment plan model development component 306 can further learn correlations between different treatment processes and/or actions and various parameters associated with the injury (e.g., severity, location, size, depth, duration, etc.), the patient (e.g., age, medical history, physiological parameters, behavior data), the context of the injury/incident, the risk information associated with the reported injury/incident, and further, the actual outcomes/patient reactions (e.g., good and bad) that occurred in response to performance of the treatment processes and/or specific actions included in the different treatment processes. Based on these learned correlations, the treatment plan model development component 306 can further develop one or more treatment plan models 308 configured to generate an "optimal" treatment plan and/or treatment actions to perform in association with responding to a newly reported incident/injury (e.g., represented by the initial incident information). The "optimal" treatment plan can be based on preferred clinical outcomes (e.g., curing or minimizing the injury), minimizing risk, minimizing costs, minimizing pain, and maximizing good outcomes, and the like. In some implementations, the treatment plan models 308 can include a different model for each (or in some implementations one or more) type of injury. Each model can further generate an optimal treatment plan or optimal treatment actions for performing that results in achieving the desired outcomes (e.g., curing or minimizing the injury, minimizing risk, minimizing costs, minimizing paint, etc.) in view of the severity level of the injury, the risk factors/score, the patient parameters, and the context of the injury/incident.

The treatment plan model application component 310 can further apply the one or more treatment plan models 308 (e.g., after they are developed and trained) to the initial incident information 102 using information 210 regarding the injury classification type and/or severity level (e.g., as determined by the injury classification component 110) and the risk information 212 to determine treatment plan information 312 for responding to a current incident/injury. For example, in some implementations, the treatment plan information 312 can include a list of treatment actions to be performed to treat the patient for the injury. For example, the list of treatment actions can include an ordered or prioritized list of treatment actions to be performed in a step by step manner. In some implementations, the treatment plan information 312 can also include the risk information 212.

Referring again to FIG. 1, the guidance component 118 can perform various functions to facilitate guiding the first aid responder or responders (e.g., which can include the patient or another person) in responding to a reported injury/incident. For example, in some implementations, the guidance component 118 can provide the treatment plan information (e.g., treatment plan information 312) determined by the treatment plan generation component 116 to the first responder at a device associated with the first responder. For example, the guidance component 118 can provide the treatment plan information for rendering at the device as text, as audio (e.g., computer generated spoken speech), as imagery and/or the like. In another example, the guidance component 118 can facilitate guiding the first aid response process via voice, video and/or augmented reality (AR) techniques using the determined treatment plan information. For instance, in one implementation, the guidance component 118 can facilitate rendering the treatment plan information using AR techniques that overlay visual information or indicators (e.g., text, symbols, images, video, animations, etc.) onto a live view of the patient, injury and/or incident environment (e.g., displayed via a heads-up display, goggles, glasses, or another AR display device). For instance, the visual information or indicators can guide the first aid responder and/or provide an example demonstration of a treatment action for performance by the first aid responder in real-time. The example demonstration can include a video and/or image data rendered via a heads-up display, goggles, classes, etc. in a manner that demonstrates where and how to treat the patient while allowing the first aid responder to maintain a live view of the patient, injury and/or incident environment. In another implementation, the guidance component 118 can provide interactive guidance information to the first aid responder using the treatment plan. For example, the guidance component 118 can receive feedback from the first aid responder requesting advice on what to do next, requesting assistance or emergency services, and the like, and the guidance component 118 can provide requested information and/or perform the requested action (e.g., contact emergency services or assistance), as requested. In some implementations, in addition to the treatment plan information, the guidance information 126 can include information identifying the injury classification and/or severity level and identifying the risk level and/or risk factors and associated probabilities of occurrence.

In various embodiments, the guidance component 118 can also access and provide additional relevant or useful information included provided by one or more injury information systems/sources 128 to facilitate responding to the injury/incident. For example, in one implementation, the guidance component 118 can provide the first responder with information (or links to information) describing the type of injury, information indicating key facts about the type of injury, information describing how common the injury is, and the like. In another implementation, the guidance component 118 can access information (e.g., included in one or more injury information systems/sources 128) identifying other individuals that have experienced a same or similar injury/incident and facilitate connecting the current first responder to those individuals for help, guidance, and support. For example, in a scenario in which the first responder is parent reporting an injury endured by the parent's pediatric patient, the guidance component 118 can access information identifying friends and/or contacts of the parent that have previously experienced a same or similar scenario in association with caring for a pediatric patient. In another example, the guidance component 118 can access information identifying other individuals (e.g., other parents) that may be unknown by the parent but have previously experienced a same or similar scenario in association with caring for a pediatric patient. In another example, the guidance component 118 can access information identifying emergency medical service (EMS) personnel and/or clinicians (e.g., doctors, nurses, etc.) who have worked on patients with same similar injuries or incidents. The guidance component 118 can further include information identifying those contacts in the guidance information 126 and in some implementation, provide links to initiate a call or send a message to the respective contacts. In another implementation, the guidance component 118 can provide the first responder with directions to the nearest clinic or medical facility where the first responder can take the patient to receive recommended care.

With reference to FIGS. 1-3, in some implementations, the computing device 104, one or more of the various components of the computing device 104, and other computing systems and data sources (e.g., the one or more injury information systems/sources 128, the historical incident information 202 datastore, the historical incident information plus risk 302 datastore, the domain knowledge treatment information 304 datastore, etc.) of system 100, system 200, system 300 (and other systems described herein) can be communicatively connected via one or more networks (not shown). In this regard, the computing device 104, one or more of the various components of the computing device 104, and other computing systems and data sources of system 100, system 200 and/or system 300 can be collocated and/or distrusted amongst different systems and/or devices/machines in a distributed computing environment and communicatively coupled via one or more networks. Such networks can include wired and wireless networks, including but not limited to, a cellular network, a wide area network (WAD, e.g., the Internet) or a local area network (LAN).

For example, using one more networks, the computing device 104 can communicate with one or more systems, devices, datastores, etc., that provide information and/or data models (e.g., the initial incident information 102, the historical incident information 202, the one or more risk models 206, the risk information 212, the historical incident information plus risk 302, the domain knowledge treatment information 304, the one or more treatment plan models 308, relevant guidance information regarding a current incident provided by the one or more injury information systems/ sources 128, and the like) that are used by the incident assessment component 108, the incident reporting component 114, the treatment plan generation component 116 and/or the guidance component 118. The computing device 104 can also communicate with one or more systems, devices, and/or datastores via one or more networks in association with providing the guidance information 126 for rendering (e.g., in real-time) and/or for storing the guidance information 126 and other information received by and/or generated by the one or more components of the computing device 104.

The computing device 104 can thus include hardware (e.g., a central processing unit (CPU), a transceiver, a decoder), software (e.g., a set of threads, a set of processes, software in execution) or a combination of hardware and software that facilitates communicating information between the computing device 104 and externals systems, sources and devices. The computing device 104 can include any suitable computing device (or group of computing devices) configured to receive and process the initial incident information 102 and/or execute the feature and functionalities of the incident assessment component 108, the treatment plan generation component 116 and/or the guidance component 118 as discussed herein. For example, the computing device 104 can be or include a server device, desktop computer, a laptop computer, a television, an Internet-enabled television, a mobile phone, a smartphone, a tablet personal computer (PC), or a personal digital assistant (PDA), a heads-up display (HUD), an augmented reality (AR) device, a virtual reality (VR) device, a wearable device, an implanted medical device (IMD), and the like.

In some implementations, the computing device 104 can be or correspond to a server device. In other implementations, the computing device 104 can be or correspond to a client device. For example, in some embodiments, one or more features and functionalities of system 100 (and additional systems described herein) can be executed using a website or web-based platform (e.g., as software as a service SAS) that can be accessed by one or more client devices using a browser. In other embodiments, one or more features and functionalities of system 100 (and additional systems described herein) can be executed using a mobile application, a thin client application, a thick client application, a hybrid application, a web-application and the like. For example, in some implementations, system 100 can employ a server-client architecture to execute the various features and functionalities of system 100. According to this example, a client device can include a dedicated application configured to perform at least some feature and functionalities of system 100 while a server device communicatively coupled to the client device can be configured to perform the other features and functionalities of system 100.

Figure 4:
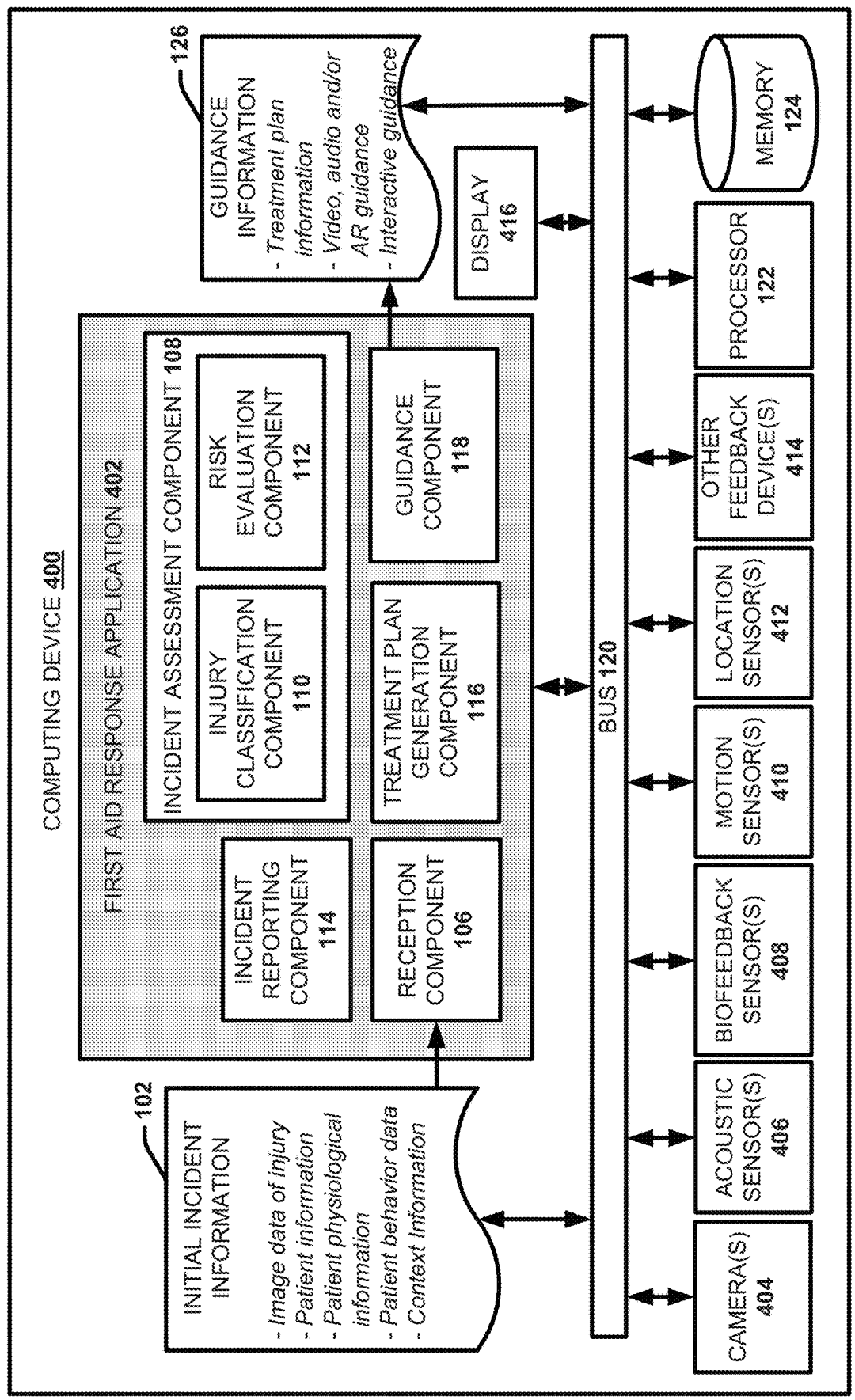
FIG. 4 illustrates a block diagram of an example, computing device comprising a system for providing live first aid response guidance using a machine learning based cognitive aid planner in accordance with one or more embodiments of the disclosed subject matter.

For example, FIG. 4 illustrates a block diagram of an example computing device 400 configured to execute one or more features and functionalities of system 100 (and other system described herein) using a first aid response application 402. Repetitive description of like elements employed in respective embodiments is omitted for sake of brevity.

In the embodiment shown, the components of system 100 are included in a first aid response application stored and/or executed by the computing device 400. For example, in some implementations, the computing device 400 can include a mobile device (e.g., a smartphone, a tablet, an AR device, a laptop PC, etc.) and the first aid response application 402 can be or correspond to a mobile application (e.g., resident on the mobile device and/or downloaded from an application server). In this regard, in some embodiments, the first aid response application 402 can perform the same features and functionalities of the corresponding components as described with reference to FIGS. 1-3. In other embodiments, one or more features and functionalities of the corresponding components can be distributed between the first aid response application 402 and a server device (not shown) communicatively coupled to the computing device 400 via one or more networks.

For example, in one implementation, the first aid response application 402 can include the incident reporting component 114 and facilitate collecting the initial incident information 102 and providing the initial incident information to the server device. The server device can, in turn, be configured to perform the processing functions of the incident assessment component 108 and the treatment plan generation component 116 and provide the resulting information to the first aid response application 402 (e.g., the injury type and severity classification information 210, the risk information 212, and/or the treatment plan information 312, and the like). The first aid response application 402 can further perform one or more features and functionalities of the guidance component 118 using the received information. In another embodiment, one or more features and functionalities of the incident assessment component 108 and/or the treatment plan generation component 116 can be distributed between the server device and the first aid response application 402. For example, the server device can perform the model training and development processing functions to develop and/or train the one or more risk models 206 and/or the one or more treatment plan models 308, and the first aid response application can apply the trained risk models 206 and/or treatment plan models 308 to the initial incident information 102.

In the embodiment shown, the computing device 400 can also include various input/output devices/sensors to facilitate generating the initial incident information 102 and/or rendering the guidance information 126. For example, the computing device 400 can include one or more cameras 404 (e.g., which can include still image and video cameras), one or more acoustic sensors 406, one or more biofeedback sensors 408 (e.g., configured to capture physiological information), one or more motion sensors 410, one or more location sensors 412, and various other feedback devices 414. The computing device 400 can also include at least one display 416 to display the guidance information. In some embodiments, the incident reporting component 114 can activate (e.g., turn on) one or more of the various sensors in association with initiation of an incident report. For example, in one implementation, the incident reporting component 114 can activate the one or more cameras 404 and/or other types of sensors in association with the opening of the first aid response application 402. In another implementation, the incident reporting component 114 can activate the one or more cameras 404 and/or other types of sensors in response to reception of user input requesting to report a new incident/injury.

In one example use case scenario involving computing device 400, in association with opening the first aid response application 402 and/or initiating a request to report an injury/incident using the first aid response application, the incident reporting component 114 can access an augmented reality application (AR) of the computing device 400 (not shown). The AR application and/or the incident reporting component 114 can further turn on one or more of the cameras 404 and direct the user to take a video and/or images of the injury (if the injury has a visual manifestation on the patient's body). Once the camera is moved over the injury and image data is received, the injury classification component 110 can classify the type and severity of the injury using one or more machine learning models (e.g., one or more CNN based models as described above). In some implementations, the guidance component 118 can further display the results to the user via the device display 416. For example, in one embodiment, the guidance component 118 can display the results as an overlay on the image data capture of the injury (e.g., using the AR application or another rendering application). Based on the injury type, its severity level, additional initial incident information regarding the patient and the context of the injury, the risk evaluation component 112 can further determine the risk information and display the results to the user. The treatment plan generation component 116 can further develop a treatment plan with first aid response actions for the first aid responder to perform. For example, the treatment plan and/or information regarding the treatment plan can be displayed on a computing device 104 or display 416. For example, the treatment plan information can include quick steps to remediate the problem as well as emotional support to calm down the patient and/or first aid responder. The guidance component 118 can further render the treatment plan information via the display 416 and/or using the one or more acoustic sensors 406 (as speech). In some implementations, the guidance component 118 can also provide additional shortcuts to call emergency services and automatically provide the emergency responders with information about the injury/incident. This could be very useful as a special burn unit might be dispatched instead of a regular ambulance. The guidance component 118 can also provide quick links to contact friends and/or family or other entities that can provide support and assistance (e.g., other patients or first aid responders who went through the same or similar experience.)

FIGS. 5A and 5B present example first aid guidance information (e.g., guidance information 126) as rendered at a mobile device (e.g., a smartphone) in association with various example use cases of the disclosed system(s) for providing live first aid response guidance in accordance with one or more embodiments of the disclosed subject matter. In some embodiments, the mobile device can be or correspond to computing device 104 and/or computing device 400. Repetitive description of like elements employed in respective embodiments is omitted for sake of brevity.

In the embodiments shown, each example use case provides an image of the injury or injuries (e.g., captured via the smartphone rendering the image), information classifying the type of the injury or injuries, and a determined severity level of the injury or injuries. For example, use case 501 depicts an injury classified as a nail tear bleeding assigns a severity level of 1 to the injury. Use case 502 depicts an injury classified as a foot cut bleeding and assigns a severity level of 2 to the injury. Use case 503 depicts burn injuries classified as sun burns and assigns a severity level of 2 and 3 to the respective injuries. Use case 504 depicts an injury classified as an electrical burn and assigns a severity level of 2 to the injury. Use case 505 depicts an injury classified as a thermal burn and assigns a severity level of 3 to the injury. Each example use case also provides links to view quick steps for responding to the injury, a link to call 911, and a link to contact other relevant entities (e.g., noted friends and family members, other support systems, etc.)

Figure 6:
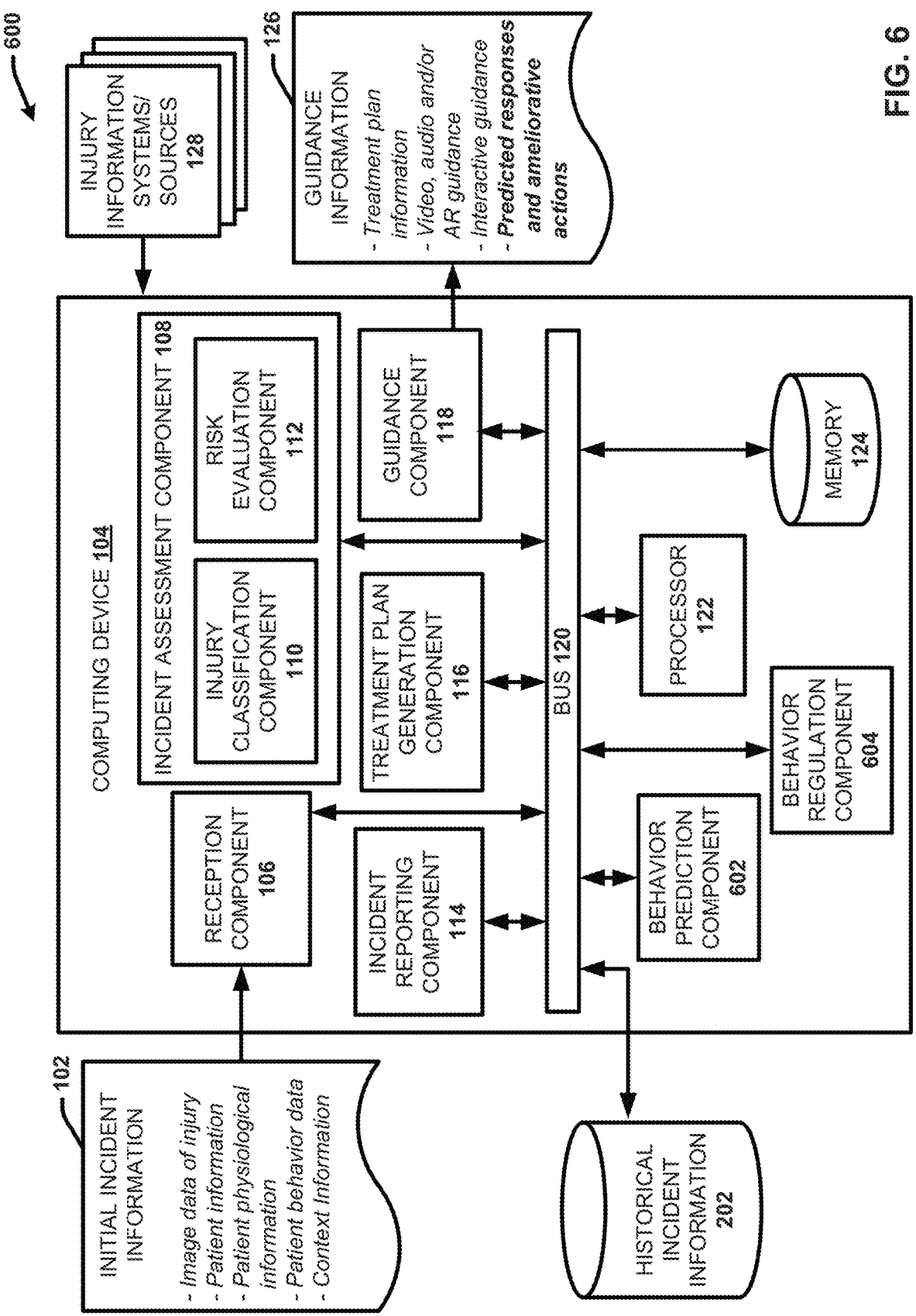
FIG. 6 illustrates a block diagram of another example, non-limiting system for providing live first aid response guidance using a machine learning based cognitive aid planner in accordance with one or more embodiments of the disclosed subject matter.

FIG. 6 illustrates a block diagram of another example, non-limiting system 600 for providing live first aid response guidance using a machine learning based cognitive aid planner in accordance with one or more embodiments of the disclosed subject matter. System 600 includes same or similar features and functionalities as system 100 with the addition of behavior prediction component 602 and behavior regulation component 604. In various embodiments, system 600 can include system 200 and/or system 300, (or vice versa). Repetitive description of like elements employed in respective embodiments is omitted for sake of brevity.

In one or more embodiments, the behavior prediction component 602 can predict one or more responses or reactions of the patient to one or more treatment actions provided in the treatment plan. For example, the behavior prediction component can predict physiological reactions (e.g., decreasing of temperature, increasing of heart rate, reduction of bleeding, etc.) of the patient as well as behavioral reactions/responses of the patient. For example, in various implementations in which the patient is a pediatric patient, the behavior prediction component 602 can predict what the pediatric patient may do in response to performance of a recommended treatment action, such as for example, cry, scream, kick, scratch, panic, attempt to remove an applied bandage, use injured limb unintentionally, etc. In accordance with these embodiments, the behavior prediction component 602 can also employ AI and/or one or more machine learning techniques to predict the patient's responses to treatment actions based on past responses to the treatment actions applied to patient's with similar profiles and/or under similar contexts. For example, the behavior prediction component 602 can evaluate the historical incident information to learn correlations between patient responses/reactions to different treatment actions and patient profile characteristics, incident context, and the like. In some implementations, the behavior prediction component 602 can develop and train one or more models for different types of treatment actions based on the learned correlations. For example, the one or more models can respectively be configured to predict a patient reaction to a treatment action based on patient profile characteristics, based on contextual factor for the incident, based on the type of the injury and/or the severity level of the injury, based on the location of the injury (on the patient's body), and the like. The behavior prediction component 602 can further apply the one or more models to predict patient reactions in live scenarios.

In some embodiments, the behavior prediction component 602 can also predict behavioral reactions/responses of the caregiver performing the treatment. For example, in furtherance to the example above in which the patient is a pediatric patient, the behavior prediction component 602 can predict how the caregiver will respond to the pediatric patient crying, screaming, kicking, etc. This might be useful if the caregiver cannot properly attend to the pediatric patient following an incident. For example, a caregiver might "freeze" at the sight of blood. The behavior prediction component 602 can employ same or similar machine learning techniques using the historical incident information 202 to predict the caregiver reactive behavior.

The behavior regulation component 604 can further determine appropriate amelioration action to regulate the predicted behavior of the patient and/or caregiver to prevent or minimize further injury. The behavior regulation component 604 can also learn the appropriate amelioration actions using one or more machine learning techniques and analysis of the historical incident information 202. The guidance component 118 can further provide information identifying the predicted responses and/or the ameliorative actions to the patient and/or entity performing or facilitating the first aid response as guidance information 126. In various embodiments, the amelioration actions can be tailored based on the patient profile and context. For example, the behavior regulation component 604 can evaluate the historical incident information 202 using one or more machine learning techniques to learn what amelioration actions work best in terms of minimizing harm and/or counteracting a particular behavioral reaction to a particular treatment action for other patients with similar profiles and/or under similar contexts.

Figure 7:
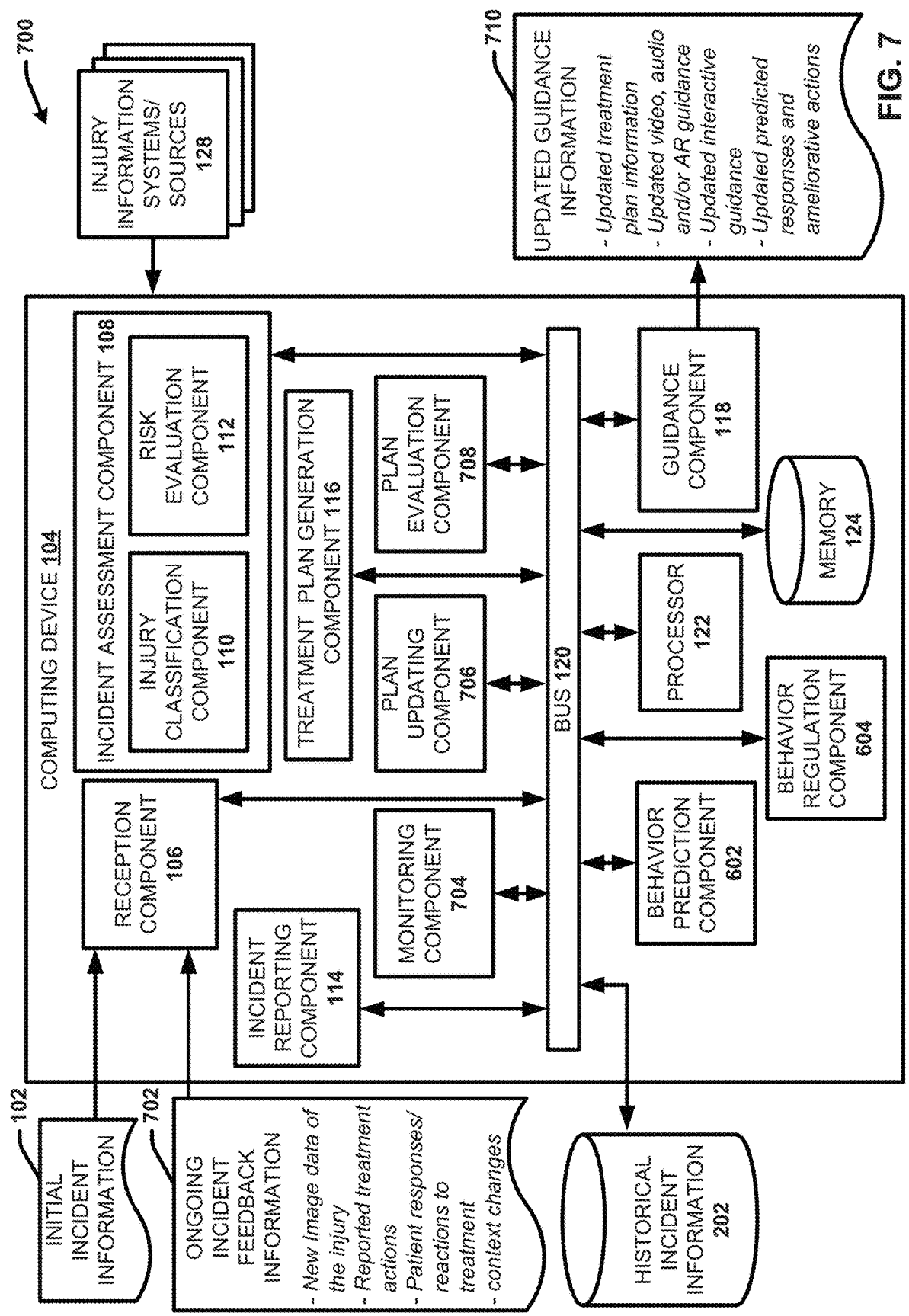
FIG. 7 illustrates a block diagram of another example, non-limiting system for providing live first aid response guidance using a machine learning based cognitive aid planner in accordance with one or more embodiments of the disclosed subject matter.

FIG. 7 illustrates a block diagram of another example, non-limiting system 700 for providing live first aid response guidance using a machine learning based cognitive aid planner in accordance with one or more embodiments of the disclosed subject matter. System 700 includes same or similar features and functionalities as system 600 with the addition of monitoring component 704, plan updating component 706 and plan evaluation component 708. In various embodiments, system 700 can include system 200 and/or system 300, (or vice versa). Repetitive description of like elements employed in respective embodiments is omitted for sake of brevity.

In one or more embodiments, the monitoring component 704 can continuously monitor and analyze a reported incident/injury after initial reporting of the incident/injury and reception of the initial incident information 102. For example, after initial reporting, the reception component 106 can continue to receive ongoing incident feedback information 702 regarding the incident/injury. The ongoing incident feedback information 702 can include the same or similar types of information included in the initial incident information. For example, the ongoing incident feedback information 702 can include new image data of the injury, patient physiological data, patient behavior data, context information, and the like. The ongoing incident feedback information 702 can also include information regarding treatment actions performed, patient responses/reactions to the treatment actions, information regarding changes to the context of the incident, and the like.

In this regard, the monitoring component 704 can continuously and/or regularly monitor the ongoing incident feedback information received over time (e.g., over a course of treatment or care of the patient) to facilitate evaluating the status of the patient/injury to determine how to continue to guide the first responder in association with treating the patient/injury. For example, in some implementations, the monitoring component 704 can direct the incident assessment component 108 to regularly or continuously determine updated injury severity level and/or risk information based on detected changes in parameters included in the ongoing incident feedback information 702 (e.g., relative to the initial incident information 102 and/or relative to previously received ongoing incident feedback information 702 at an earlier point in time). The treatment plan generation component 116 can further regularly and/or continuously generate new treatment plan information based on the changed parameters/parameter values reflected in the ongoing incident feedback information 702 and the updated injury severity level and/or risk information.

In some embodiments, the plan updating component 706 can further evaluate the new treatment plan information in view of the previously determined treatment plan information to determine any changes to the previously determined treatment plan and/or new treatment actions to perform. Based on the identification of changes and/or new treatment plan actions, the plan updating component 706 can further generate updated treatment plan information including the changes and/or new treatment plan actions. The guidance component 118 can further generate and provide the first responder with updated guidance information 710 based on the update treatment plan information. For example, the updated guidance information 710 can include the updated treatment plan, updated video, audio and/or AR guidance, updated interactive guidance, updated predicted responses and ameliorative actions, and the like.

The plan evaluation component 708 can further provide for evaluating the effectiveness of the recommended treatment plan actions based on the ongoing incident feedback information 702. For example, the plan evaluation component 708 can evaluate the guidance provided to the caregiver(s) during the course of regulating the incident, and actions that were performed by the caregiver(s) in association with the initially provided guidance information 126 and/or the updated guidance information 710. The plan evaluation component 708 can also regularly or continuously evaluated changes in the ongoing incident feedback information 702 and/or the updated severity level and/or risk information to determine whether and to what degree the treatment plan actions are alleviating the injury other otherwise improving the status/state of the patient/injury. In some implementations, based on a determination that one or more treatment actions are not resulting in sufficient improvement to the patient/injury (e.g., relative to a defined performance metric), the plan evaluation component 708 can direct the plan updating component 706 to determine alternative or updated treatment actions based on the ongoing incident feedback information and the previously performed treatment actions. In various additional implementations, the plan evaluation component 708 can analyze the effectiveness of a recommended treatment plan based on the ongoing incident feedback information 702 and historical treatment plans based on similarity analysis.

In some embodiments, the plan evaluation component 708 can further prompt the first responder to provide feedback regarding whether the suggested treatment actions are improving the patient's current condition. Based on the response provided by the first responder, the plan evaluation component 708 can direct the incident assessment component 108 and the treatment plan generation component 116 to re-evaluate the incident/injury by pulling together additional feedback information for the incident/injury (e.g., the ongoing incident feedback information 702). For example, the plan evaluation component 708 can direct the incident reporting component 114 to generate/collect additional images of the injury, additional physiological data for the patient, additional context information, and the like.

Figure 8:
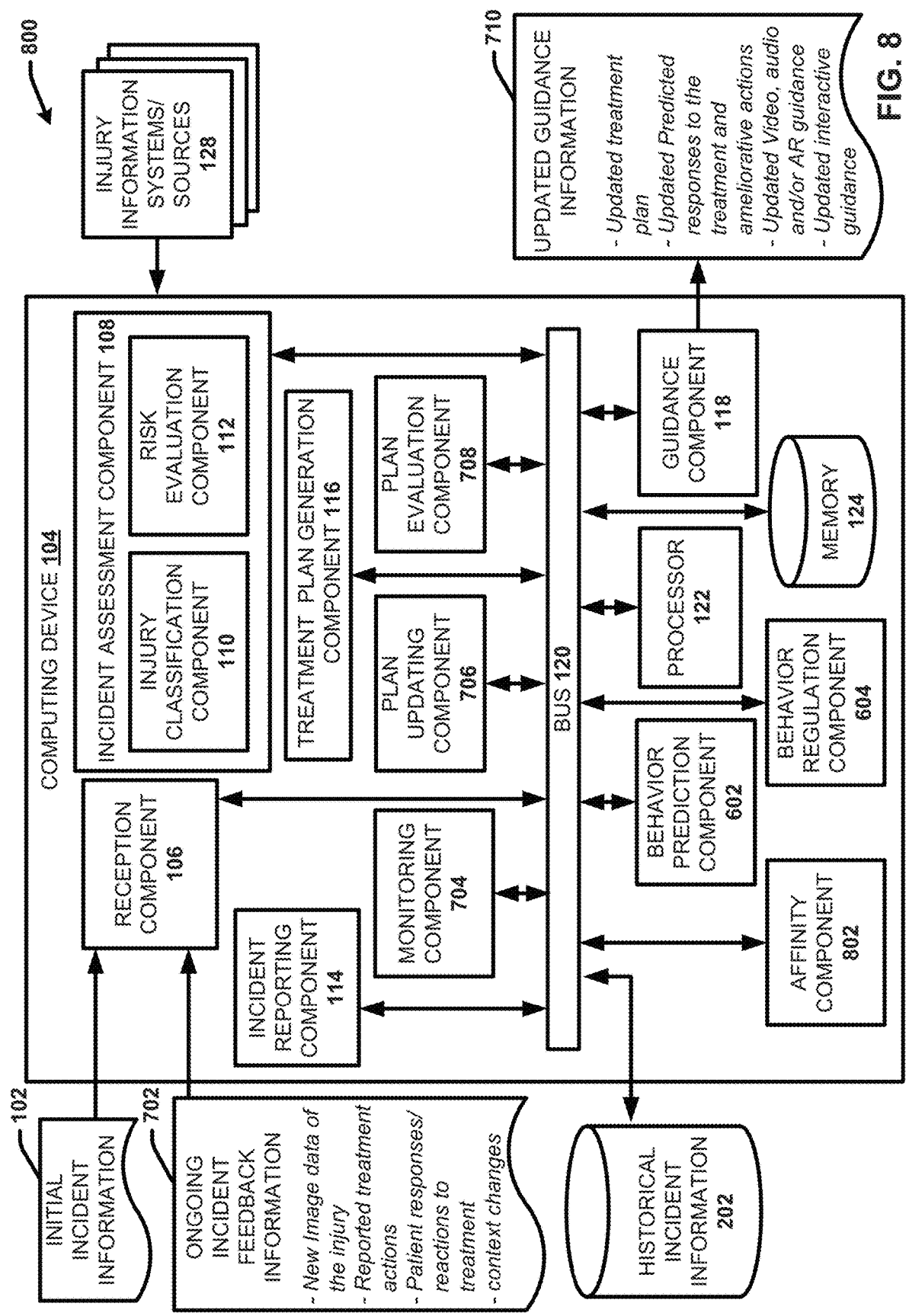
FIG. 8 illustrates a block diagram of another example, non-limiting system for providing live first aid response guidance using a machine learning based cognitive aid planner in accordance with one or more embodiments of the disclosed subject matter.

FIG. 8 illustrates a block diagram of another example, non-limiting system 800 for providing live first aid response guidance using a machine learning based cognitive aid planner in accordance with one or more embodiments of the disclosed subject matter. System 800 includes same or similar features and functionalities as system 700 with the addition of affinity component 802. In various embodiments, system 800 can include system 200 and/or system 300, (or vice versa). Repetitive description of like elements employed in respective embodiments is omitted for sake of brevity.

In one or more embodiments, the affinity component 802 can learn the preferences of specific patients and/or different patient groups regarding their affinities toward different treatment actions. For example, with respect to a specific patient, the affinity component 802 can evaluate how the patient' responds to different treatment actions with respect to the patient's behavior and/or mood (e.g., either in a favorable or unfavorable manner). For instance, the affinity component 802 can learn what types of treatment actions or treatment delivery techniques the patient responds positively too (e.g., by smiling, not crying, not complaining, etc.), and what techniques the patient responds negatively too (e.g., by frowning, crying, complaining, etc.) based on analysis of the ongoing incident feedback information 702. In this regard, in various embodiments, the monitoring component 704 can monitor feedback information (e.g., included with the ongoing incident feedback information 702) regarding the behavior of a patient in association with treatment of the patient based on the recommended treatment plan. The affinity component 802 can further estimate one or more affinities of the patient related to the treatment based on the monitored feedback information. For example, in some implementations, the feedback information can include interaction data captured via one or more sensors (e.g., one or more cameras 404, one or more acoustic sensors 406, one or more biofeedback sensors 408, one or more motion sensors 410 and other feedback devices 414) regarding interaction between the patient and one or more entities that provide or facilitate the treatment. The feedback information can also comprise reaction data captured via the one or more sensors regarding one or more reactions of the patient to the treatment. For example, in some implementations, the affinity component 802 can evaluate how the patient is responding to treatment actions and/or interacting with a caregiver based on tracking the patient's eyes (e.g., using one or more eye-tracking sensory), based on tracking the patient's motion, based on tracking the patient's speech, and the like.

The treatment plan generation component 116 can further tailor the recommended treatment actions and/or guidance information based on the learned patient affinities. For example, when generating subsequent treatment plan information for treating that particular patient (e.g., further current incident/injury or a new injury/incident reported at a later time), the treatment plan generation component 116 can include the types of treatment actions that the patient responds positively too as opposed to those that the patient responds negatively too. In addition, the affinity component 802 can develop affinity profiles for different groups of people with different profiles (e.g., grouped by age, geographic region, activity level, development stage, hobbies, etc.). The affinity profiles can reflect the learned affinities toward different treatment actions for the different patient groups. The treatment plan generation component 116 can further employ the affinity profiles in association with determining treatment actions for a new patient fitting one or more of the patient profiles.

Figure 9:
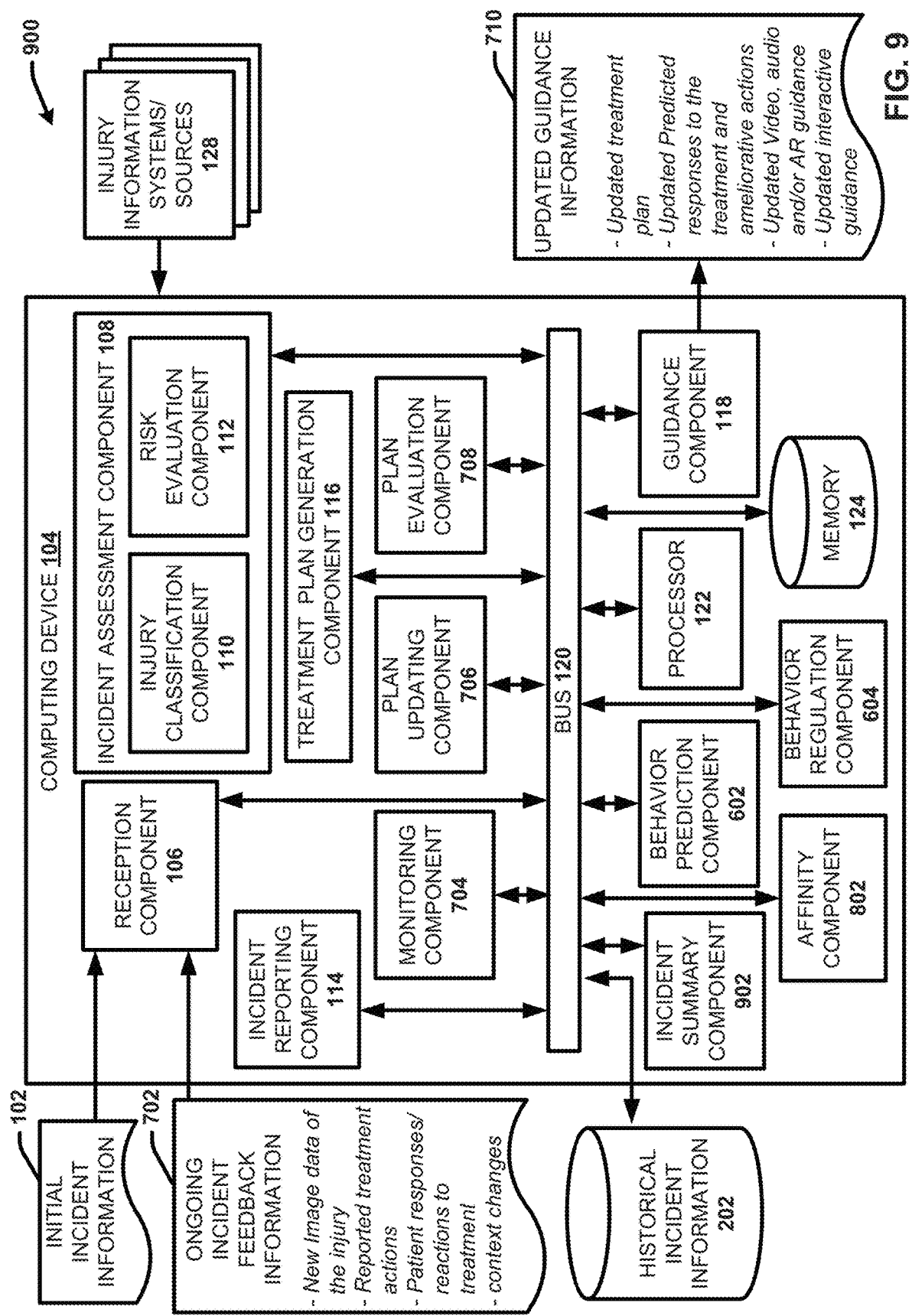
FIG. 9 illustrates a block diagram of another example, non-limiting system for providing live first aid response guidance using a machine learning based cognitive aid planner in accordance with one or more embodiments of the disclosed subject matter.

FIG. 9 illustrates a block diagram of another example, non-limiting system 900 for providing live first aid response guidance using a machine learning based cognitive aid planner in accordance with one or more embodiments of the disclosed subject matter. System 900 includes same or similar features and functionalities as system 800 with the addition of incident summary component 902. In various embodiments, system 900 can include system 200 and/or system 300, (or vice versa). Repetitive description of like elements employed in respective embodiments is omitted for sake of brevity.

In various embodiments, system 900 and additional systems described herein can be used to provide first aid response guidance for many different patients for many different types of injuries/incidents. For example, in some embodiments in which the disclosed systems are deployed using a mobile application platform, essentially any individual having a mobile device can employ the first aid application to facilitate reporting and receiving guidance for injuries/incident that occur in their daily lives, either as a patient or a caregiver/entity facilitating a first aid response for another individual (e.g., their pediatric patient, a friend or family member, or themselves, etc.). In this regard, as new incidents/injuries are reported and processed over time to generate guidance information in accordance with the techniques described herein, the disclosed systems can generate massive amounts of new historical incident information 202. In various embodiments, the risk model development component 204, the treatment plan model development component 306, the behavior prediction component 602, the behavior regulation component 604, the plan evaluation component 708 and the affinity component 802 can regularly process the new historical data to optimize the predictive accuracy and specificity of the respective components. For example, the risk model development component 204 can employ the new historical incident data to optimize the one or more risk models 206 and/or generate new risk models over time. Likewise, the treatment plan model development component 306 can employ the new historical incident data to optimize the one or more treatment plan models over time.

The incident summary component 902 can facilitate the collecting and aggregating of the new historical incident data over time and add additional information to the historical incident information 202. For example, each time (or in some implementations one or more) an incident/injury is reported and processed by system 900 (and other systems described herein) using the various techniques described herein, a plethora of rich information about the incident/injury, the first aid response provided and the patient reactions to the first aid response can be generated. In one or more embodiments, the incident summary component 902 can generate an incident summary for each reported incident aggregating and summarizing the relevant information. The incident summary component 902 can further add the incident summary report to the historical incident information for continued machine learning optimization.

Figure 10:
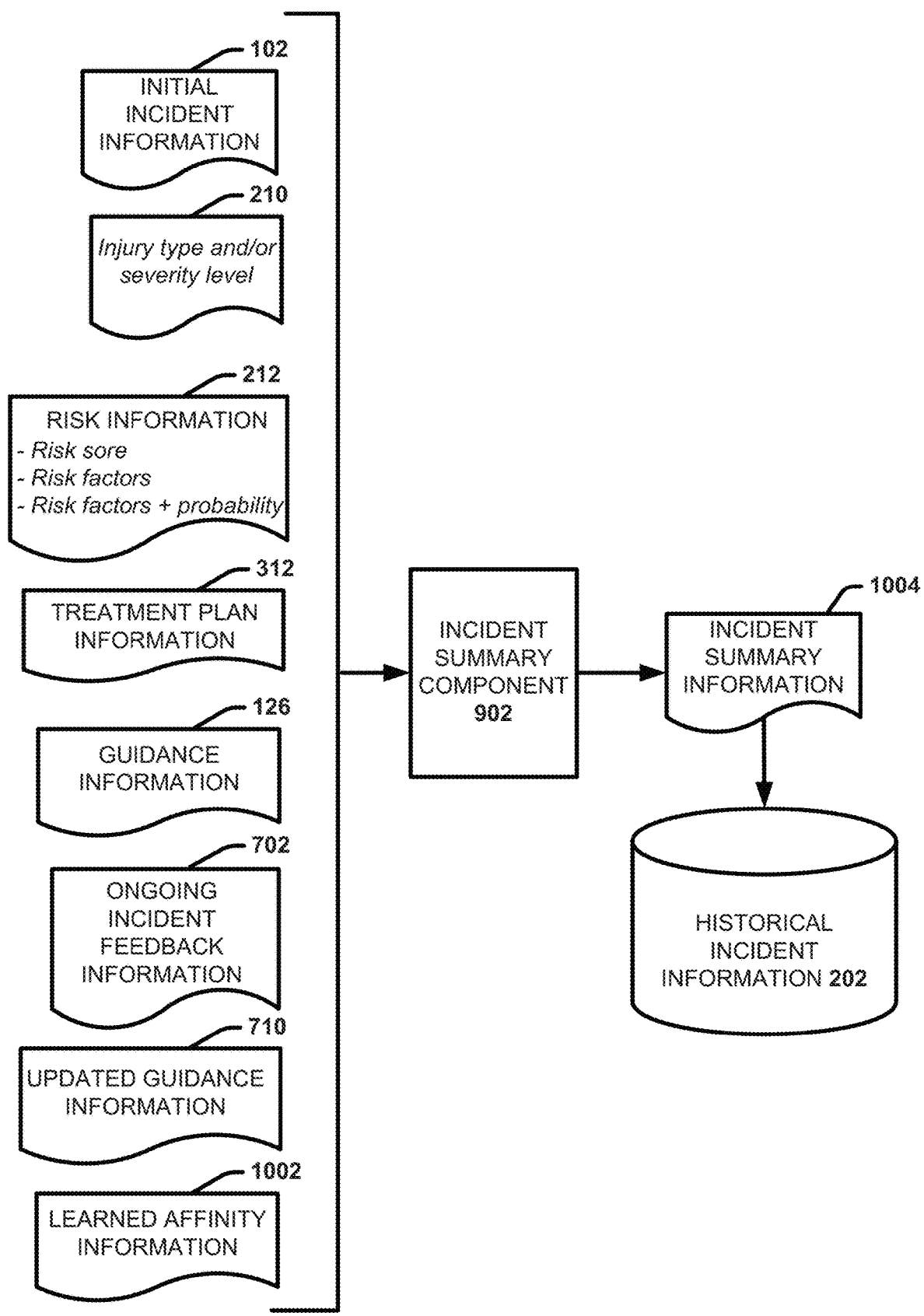
FIG. 10 illustrates the various types of information that can be collected and combined regarding a reported incident and added to historical incident information in accordance with one or more embodiments of the disclosed subject matter.

For example, FIG. 10 illustrates the various types of information that can be collected and combined for a reported incident and added to historical incident information 202 in accordance with one or more embodiments of the disclosed subject matter. As shown in FIG. 10, the incident summary component 902 can collect and aggregate the initial incident information 102, the injury type and/or severity level information 210, the risk information 212, the treatment plan information 312, the guidance information 126, the ongoing incident feedback information 702, the updated guidance information 710, and learned affinity information 1002 (e.g., determined by the affinity component 802). The incident summary component 902 can further generate incident summary information 1004 that summarizes all of the collected information and add the incident summary information 1004 to the historical information.

Figure 11:
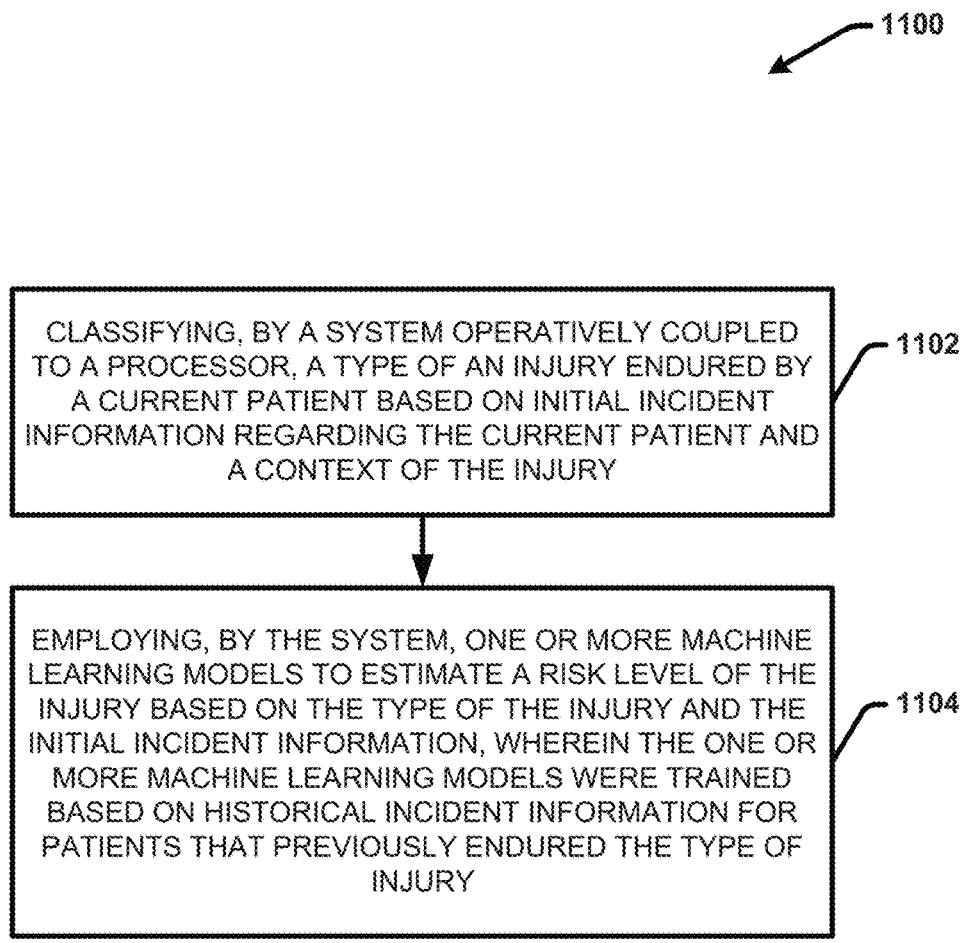
FIG. 11 illustrates an example, high-level flow diagram of a computer-implemented process for providing live first aid response guidance using a machine learning based cognitive aid planner in accordance with one or more embodiments of the disclosed subject matter.

FIG. 11 illustrates an example, high-level flow diagram of a computer-implemented process 1100 for providing live first aid response guidance using a machine learning based cognitive aid planner in accordance with one or more embodiments of the disclosed subject matter. Repetitive description of like elements employed in other embodiments described herein is omitted for sake of brevity.

At 1102, a system operatively coupled to a processor (e.g., system 100, 600, 700, 800, 900 or the like) can classify a type of an injury endured by a current patient based on initial incident information (e.g., initial incident information 102) regarding the current patient and a context of the injury (e.g., using injury classification component 110). At 1104, the system can employ one or more machine learning models (e.g., one or more risk models 206) to estimate a risk level of the injury based on the type of the injury and the initial incident information (e.g., using risk evaluation component 112), wherein the one or more machine learning models were trained (e.g., by risk model development component 204) based on historical incident information for patients that previously endured the type of injury.

Figure 12:
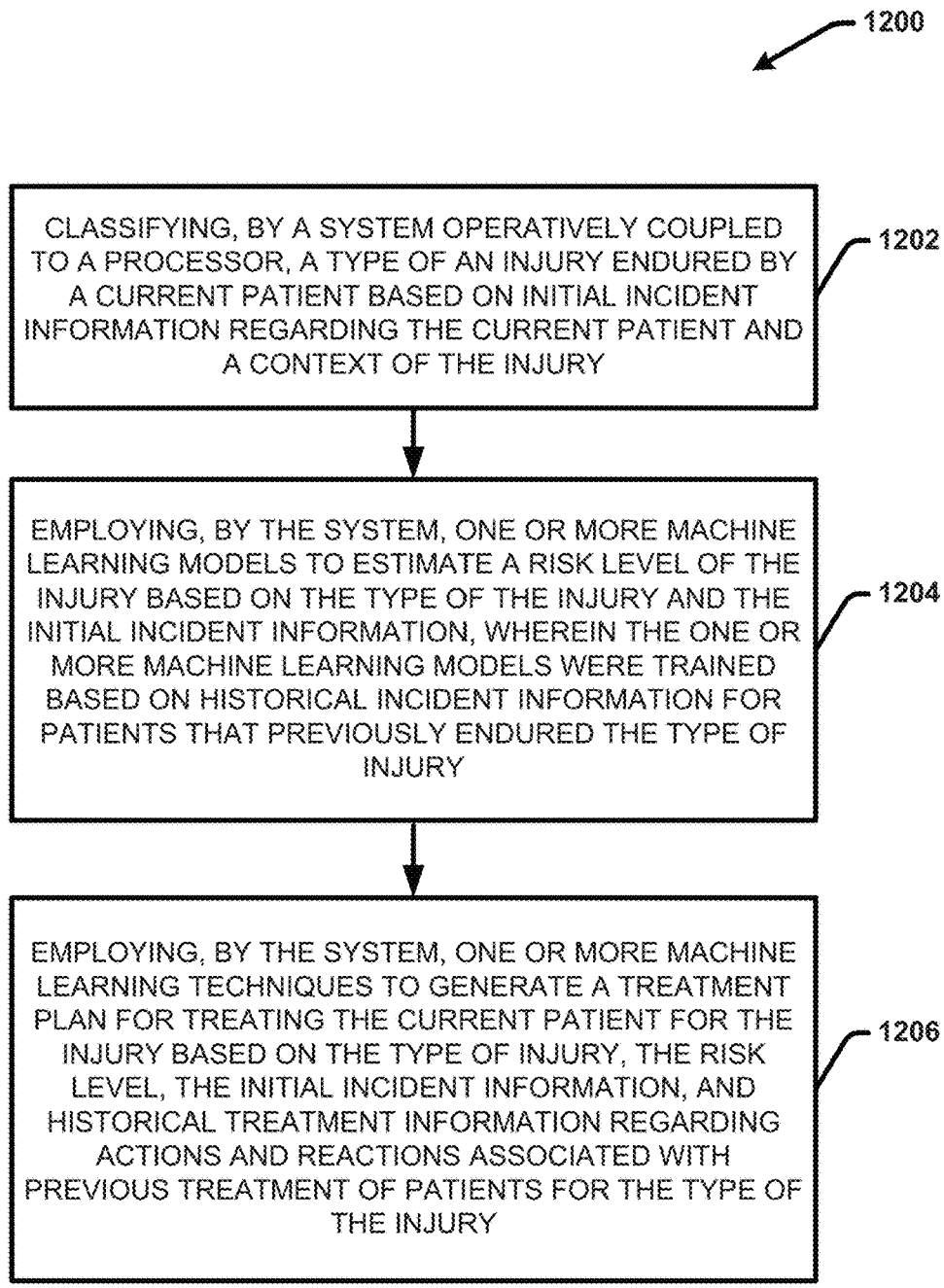
FIG. 12 illustrates another example, high-level flow diagram of a computer-implemented process for providing live first aid response guidance using a machine learning based cognitive aid planner in accordance with one or more embodiments of the disclosed subject matter.

FIG. 12 illustrates another example, high-level flow diagram of a computer-implemented process 1200 for providing live first aid response guidance using a machine learning based cognitive aid planner in accordance with one or more embodiments of the disclosed subject matter. Repetitive description of like elements employed in other embodiments described herein is omitted for sake of brevity.

At 1202, a system operatively coupled to a processor (e.g., system 100, 600, 700, 800, 900 or the like) can classify a type of an injury endured by a current patient based on initial incident information (e.g., initial incident information 102) regarding the current patient and a context of the injury (e.g., using injury classification component 110). At 1204, the system can employ one or more machine learning models (e.g., one or more risk models 206) to estimate a risk level of the injury based on the type of the injury and the initial incident information (e.g., using risk evaluation component 112), wherein the one or more machine learning models were trained (e.g., by risk model development component 204) based on historical incident information for patients that previously endured the type of injury. At 1206, the system can employ one or more machine learning techniques to generate a treatment plan for treating the current patient for the injury based on the type of injury, the risk level, the initial incident information, and historical treatment information regarding actions and reactions associated with previous treatment of patients for the type of the injury (e.g., via the treatment plan generation component 116).

Figure 13:
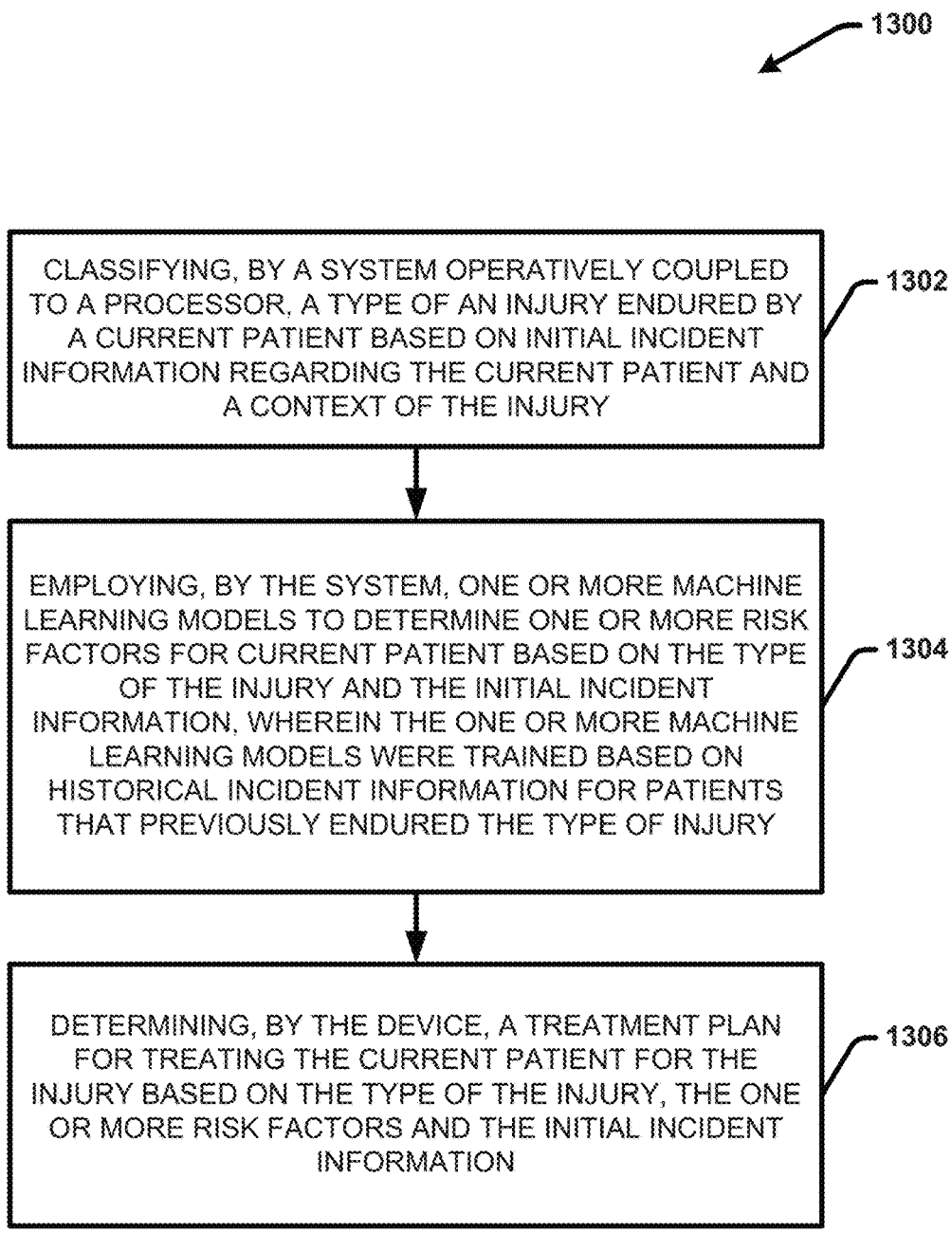
FIG. 13 illustrates another example, high-level flow diagram of a computer-implemented process for providing live first aid response guidance using a machine learning based cognitive aid planner in accordance with one or more embodiments of the disclosed subject matter.

FIG. 13 illustrates another example, high-level flow diagram of a computer-implemented process 1300 for providing live first aid response guidance using a machine learning based cognitive aid planner in accordance with one or more embodiments of the disclosed subject matter. Repetitive description of like elements employed in other embodiments described herein is omitted for sake of brevity.

At 1302, a system operatively coupled to a processor (e.g., system 100, 600, 700, 800, 900 or the like) can classify a type of an injury endured by a current patient based on initial incident information regarding the current patient and a context of the injury (e.g., using injury classification component 110). At 1304, the system can employ one or more machine learning models to determine one or more risk factors for current patient based on the type of the injury and the initial incident information (e.g., using the risk evaluation component 112), wherein the one or more machine learning models were trained based on historical incident information for patients that previously endured the type of injury. At 1306, the system can determine a treatment plan for treating the current patient for the injury based on the type of the injury, the one or more risk factors and the initial incident information (e.g., using treatment plan generation component 116).

One or more embodiments can be a system, a method, and/or a computer program product at any possible technical detail level of integration. The computer program product can include a computer readable storage medium (or media) having computer readable program instructions thereon for causing a processor to carry out one or more aspects of the present embodiments.

Figure 14:
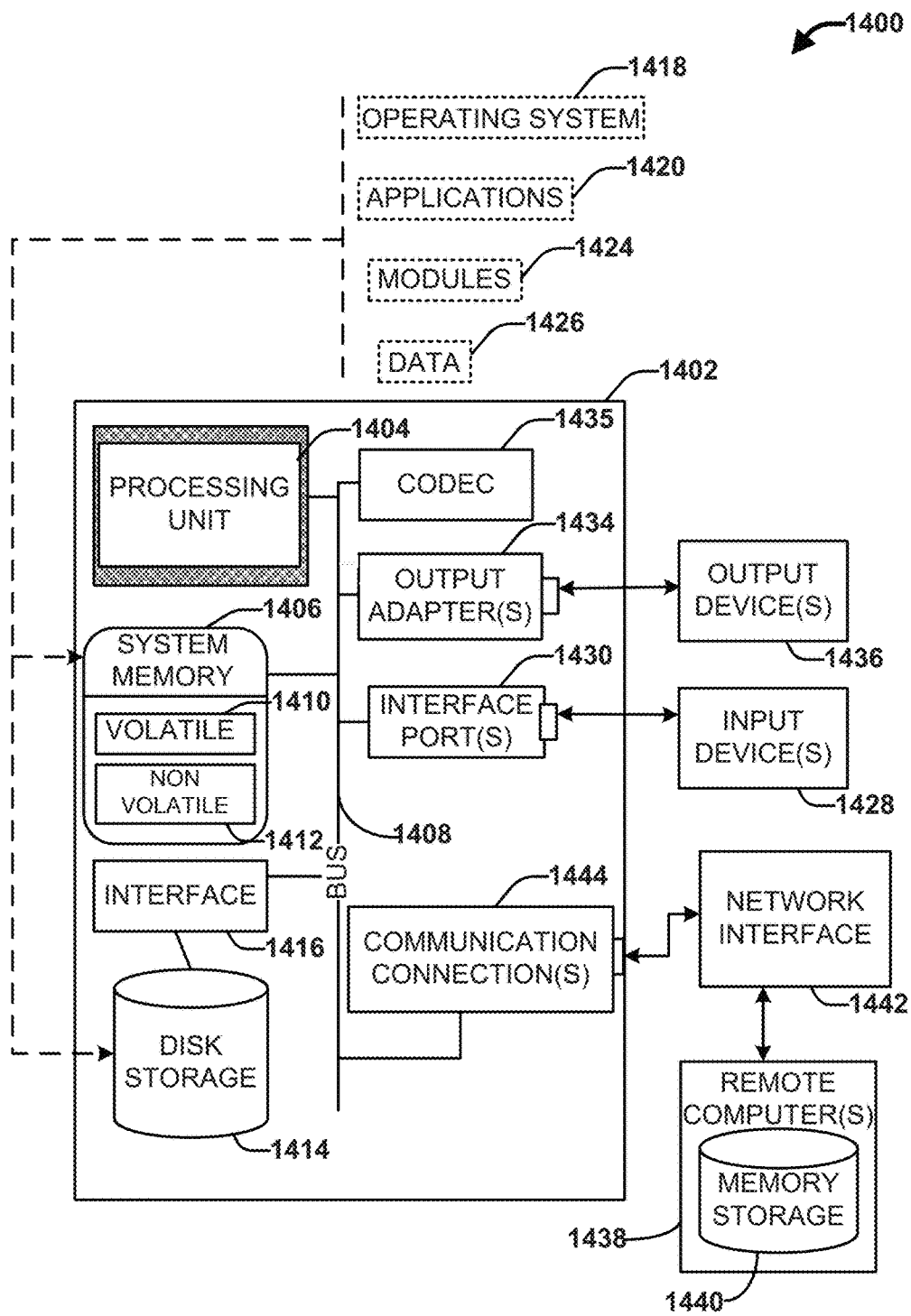
FIG. 14 illustrates a block diagram of an example, non-limiting operating environment in which one or more embodiments described herein can be facilitated.

In order to provide additional context for various embodiments described herein, FIG. 14 and the following discussion are intended to provide a general description of a suitable computing environment 1400 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices. The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 14, the example environment 1400 for implementing various embodiments of the aspects described herein includes a computer 1402, the computer 1402 including a processing unit 1404, a system memory 1406 and a system bus 1408. The system bus 1408 couples system components including, but not limited to, the system memory 1406 to the processing unit 1404. The processing unit 1404 can be any of various commercially available processors. Dual microprocessors and other multi-processor architectures can also be employed as the processing unit 1404.

The system bus 1408 can be any of several types of bus structure that can further interconnect to a memory bus (with or without a memory controller), a peripheral bus, and a local bus using any of a variety of commercially available bus architectures. The system memory 1406 includes ROM 1410 and RAM 1412. A basic input/output system (BIOS) can be stored in a non-volatile memory such as ROM, erasable programmable read only memory (EPROM), EEPROM, which BIOS contains the basic routines that help to transfer information between elements within the computer 1402, such as during startup. The RAM 1412 can also include a high-speed RAM such as static RAM for caching data.

The computer 1402 further includes an internal hard disk drive (HDD) 1414 (e.g., EIDE, SATA), one or more external storage devices 1416 (e.g., a magnetic floppy disk drive (FDD) 1416, a memory stick or flash drive reader, a memory card reader, etc.) and an optical disk drive 1420 (e.g., which can read or write from a CD-ROM disc, a DVD, a BD, etc.). While the internal HDD 1414 is illustrated as located within the computer 1402, the internal HDD 1414 can also be configured for external use in a suitable chassis (not shown). Additionally, while not shown in environment 1400, a solid state drive (SSD) could be used in addition to, or in place of, an HDD 1414. The HDD 1414, external storage device(s) 1416 and optical disk drive 1420 can be connected to the system bus 1408 by an HDD interface 1424, an external storage interface 1426 and an optical drive interface 1428, respectively. The interface 1424 for external drive implementations can include at least one or both of Universal Serial Bus (USB) and Institute of Electrical and Electronics Engineers (IEEE) 1494 interface technologies. Other external drive connection technologies are within contemplation of the embodiments described herein.

The drives and their associated computer-readable storage media provide nonvolatile storage of data, data structures, computer-executable instructions, and so forth. For the computer 1402, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1412, including an operating system 1430, one or more application programs 1432, other program modules 1434 and program data 1436. All or portions of the operating system, applications, modules, and/or data can also be cached in the RAM 1412. The systems and methods described herein can be implemented utilizing various commercially available operating systems or combinations of operating systems.

Computer 1402 can optionally comprise emulation technologies. For example, a hypervisor (not shown) or other intermediary can emulate a hardware environment for operating system 1430, and the emulated hardware can optionally be different from the hardware illustrated in FIG. 14. In such an embodiment, operating system 1430 can comprise one virtual machine (VM) of multiple VMs hosted at computer 1402. Furthermore, operating system 1430 can provide runtime environments, such as the Java runtime environment or the .NET framework, for applications 1432. Runtime environments are consistent execution environments that allow applications 1432 to run on any operating system that includes the runtime environment. Similarly, operating system 1430 can support containers, and applications 1432 can be in the form of containers, which are lightweight, standalone, executable packages of software that include, e.g., code, runtime, system tools, system libraries and settings for an application.

Further, computer 1402 can be enable with a security module, such as a trusted processing module (TPM). For instance with a TPM, boot components hash next in time boot components, and wait for a match of results to secured values, before loading a next boot component. This process can take place at any layer in the code execution stack of computer 1402, e.g., applied at the application execution level or at the operating system (OS) kernel level, thereby enabling security at any level of code execution.

A user can enter commands and information into the computer 1402 through one or more wired/wireless input devices, e.g., a keyboard 1438, a touch screen 1440, and a pointing device, such as a mouse 1442. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1404 through an input device interface 1444 that can be coupled to the system bus 1408, but can be connected by other interfaces, such as a parallel port, an IEEE 1494 serial port, a game port, a USB port, an IR interface, a BLUETOOTH® interface, etc.

A monitor 1446 or other type of display device can be also connected to the system bus 1408 via an interface, such as a video adapter 1448. In addition to the monitor 1446, a computer typically includes other peripheral output devices (not shown), such as speakers, printers, etc.

The computer 1402 can operate in a networked environment using logical connections via wired and/or wireless communications to one or more remote computers, such as a remote computer(s) 1450. The remote computer(s) 1450 can be a workstation, a server computer, a router, a personal computer, portable computer, microprocessor-based entertainment appliance, a peer device or other common network node, and typically includes many or all of the elements described relative to the computer 1402, although, for purposes of brevity, only a memory/storage device 1452 is illustrated. The logical connections depicted include wired/wireless connectivity to a local area network (LAN) 1454 and/or larger networks, e.g., a wide area network (WAN) 1456. Such LAN and WAN networking environments are commonplace in offices and companies, and facilitate enterprise-wide computer networks, such as intranets, all of which can connect to a global communications network, e.g., the Internet.

When used in a LAN networking environment, the computer 1402 can be connected to the local network 1454 through a wired and/or wireless communication network interface or adapter 1458. The adapter 1458 can facilitate wired or wireless communication to the LAN 1454, which can also include a wireless access point (AP) disposed thereon for communicating with the adapter 1458 in a wireless mode.

When used in a WAN networking environment, the computer 1402 can include a modem 1460 or can be connected to a communications server on the WAN 1456 via other means for establishing communications over the WAN 1456, such as by way of the Internet. The modem 1460, which can be internal or external and a wired or wireless device, can be connected to the system bus 1408 via the input device interface 1444. In a networked environment, program modules depicted relative to the computer 1402 or portions thereof, can be stored in the remote memory/storage device 1452. It will be appreciated that the network connections shown are example and other means of establishing a communications link between the computers can be used.

When used in either a LAN or WAN networking environment, the computer 1402 can access cloud storage systems or other network-based storage systems in addition to, or in place of, external storage devices 1416 as described above. Generally, a connection between the computer 1402 and a cloud storage system can be established over a LAN 1454 or WAN 1456 e.g., by the adapter 1458 or modem 1460, respectively. Upon connecting the computer 1402 to an associated cloud storage system, the external storage interface 1426 can, with the aid of the adapter 1458 and/or modem 1460, manage storage provided by the cloud storage system as it would other types of external storage. For instance, the external storage interface 1426 can be configured to provide access to cloud storage sources as if those sources were physically connected to the computer 1402.

The computer 1402 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

What is claimed is:

1. A system, comprising:
   a memory that stores computer executable components;
   a processor that executes the computer executable components stored in the memory, wherein the computer executable components comprise:
   an incident reporting component that activates one or more sensors that gathers audio information and video data for a patient that has endured an injury and causes an incident report for the injury endured by the patient to be initiated based on collection of the audio information and the video data by the one or more sensors and electronically attaching to the system, via a computer network between a device having the one or more sensors and the system, the audio information to the system;
   an injury classification component that classifies a type of the injury endured by the patient;
   a risk evaluation component that employs one or more machine learning models to estimate a risk level associated with the injury, based on the type of the injury and on context information regarding the patient;
   an affinity component that determines one or more affinities of the patient related to a treatment plan for the injury, the one or more affinities being based on one or more monitored behavioral reactions of the patient to the treatment plan that occur during treatment of the patient, wherein the one or more behavioral reactions comprises monitored body movements of the patient, wherein the one or more machine learning models comprise a time information fusion-based approach for the video data, wherein the video data is considered a plurality of fixed-sized segments and the one or more machine learning models extend connectivity of a network in time dimension to learn spatio-temporal features for classification based on a plurality of connectivity patterns comprising early fusion, slow fusion or late fusion.

2. The system of claim 1, wherein the computer executable components further comprise:
   a treatment plan generation component that employs the one or more machine learning models to determine the treatment plan for treating the patient, based at least on the injury classification, the risk evaluation or both.

3. The system of claim 1, wherein the computer executable components further comprise:
   a guidance component that conveys, in a format observable by a treating entity, one or more updates to the treatment plan to a device to be observed by the treating entity.

4. The system of claim 1, wherein the computer executable components further comprise:
   a behavior prediction component that predicts the one or more behavioral reactions for the patient based on the treatment plan and provision of the treatment plan.

5. The system of claim 4, wherein the executable components further comprise:

a behavior regulation component that determines one or more responsive actions to minimize harm to the patient attributable to the one or more behavioral reactions; and a plan updating component that generates one or more updates to the treatment plan, based on the one or more responsive actions.

6. The system of claim 4, wherein the behavior prediction component further predicts one or more behavioral reactions for a treating entity facilitating the treatment plan, the prediction being based on one or more of the treatment plan, context information regarding the treating entity, or context information regarding the patient.

7. The system of claim 1, wherein the computer executable components further comprise:

a plan updating component that generates, during treatment of the patient according to the treatment plan, one or more updates to the treatment plan, based on the one or more affinities of the patient.

8. The system of claim 1, wherein the computer executable components further comprise:

a monitoring component that monitors feedback information regarding the one or more behavioral reactions of the patient response to facilitation of the treatment plan, wherein the affinity component employs the feedback information to determine the one or more affinities.

9. The system of claim 8, wherein the feedback information comprises interaction data captured via one or more sensors regarding one or more interactions between the patient and one or more treating entities that facilitate treatment according to the treatment plan.

10. The system of claim 1, wherein the affinity component further determines, during the treatment of the patient according to the treatment plan, the one or more affinities of the patient related to the treatment plan.

11. The system of claim 1, wherein the affinity component further determines one or more affinities of the patient related to the treatment plan, based on one or more physiological reactions of the patient to the treatment plan.

12. The system of claim 1, wherein the risk evaluation component further employs the one or more machine learning models to estimate a risk level associated with the injury, based on context information regarding a treating entity facilitating the treatment plan.

13. The system of claim 1, wherein the guidance component further accesses and provides treatment plan information or guidance to a treating entity identified as a friend, family member or contact of a treating entity facilitating the treatment plan, or guidance to a patient treated by a treating entity identified as a friend, family member or contact of the treating entity.

14. A computer implemented method, comprising:

activating, by a system operatively coupled to a processor, one or more sensors in association with initiation of an incident report for an injury endured by a patient;

classifying, by the system, a type of the injury endured by the patient;

employing, by the system, one or more machine learning models that analyzes electronic video data associated with the incident report to estimate a risk level associated with the injury based on the type of the injury and on context information regarding the patient;

determining, by the system, one or more affinities of the patient related to a treatment plan for the injury, the one or more affinities being based on one or more monitored behavioral reactions of the patient to the treatment plan that occur during treatment of the patient according to the treatment plan, wherein the one or more behavioral reactions comprises monitored body movements, wherein the one or more machine learning models comprise a time information fusion-based approach for the electronic video data, wherein the electronic video data is considered a plurality of fixed-sized segments and the one or more machine learning models extend connectivity of a network in time dimension to learn spatio-temporal features for classification based on a plurality of connectivity patterns comprising early fusion, slow fusion or late fusion.

15. The method of claim 14, further comprising:

generating, by the system, during treatment of the patient according to the treatment plan, one or more updates to the treatment plan, based on the one or more affinities of the patient.

16. The method of claim 14, further comprising:

predicting, by the system, the one or more behavioral reactions for the patient based on the treatment plan and provision of the treatment plan.

17. The method of claim 16, further comprising:

determining, by the system, one or more responsive actions to minimize harm to the patient attributable to the one or more behavioral reactions; and generating, by the system, one or more updates to the treatment plan, based on the one or more responsive actions.

18. The computer-implemented method of claim 14, further comprising:

rendering, by the system, the treatment plan information using augmented reality techniques that overlay visual information or indicators onto a live view of the patient or incident environment, wherein the rendering is via a heads-up display, goggles, glasses, or another augmented reality display device.

19. A computer program product for facilitating treating a patient for an injury, the computer program product comprising a computer readable storage medium having program instructions embodied therewith, the program instructions executable by a processing component to cause the processing component to:

activate, by the processing component, one or more sensors in association with initiation of an incident report for the injury endured by the patient;

classify, by the processing component, a type of the injury endured by the patient, wherein the type of injury is based on collected data, and wherein the collected data comprises at least video data;

employ, by the processing component, one or more machine learning models to estimate a risk level associated with the injury based on the type of the injury and on context regarding the patient;

determine, by the processing component, one or more affinities of the patient related to a treatment plan for the injury, the one or more affinities being based on one or more monitored behavioral reactions of the patient to the treatment plan that occur during treatment of the patient according to the treatment plan, wherein the one or more behavioral reactions comprises monitored eye movements determined by eye tracking sensors;

receive, by the processing component, electronic transmission of the treatment plan to a location associated with the patient, wherein the electronic treatment plan is received in the form of a text message or computer generated audio, wherein the one or more machine learning models comprise a time information fusion-based approach for the video data, wherein the video data is considered a plurality of fixed-sized segments and the one or more machine learning models extend connectivity of a network in time dimension to learn spatio-temporal features for classification based on a plurality of connectivity patterns comprising early fusion, slow fusion or late fusion.

* * * * *